(12) United States Patent
Arad (Abboud) et al.

(10) Patent No.: US 10,226,210 B2
(45) Date of Patent: Mar. 12, 2019

(54) DIAGNOSTIC AND MONITORING ELECTRICAL IMPEDANCE TOMOGRAPHY (EIT) SYSTEM FOR OSTEOPOROSIS

(71) Applicant: OsteoSee Ltd., Modiin Ilit (IL)

(72) Inventors: Shimon Arad (Abboud), Tel-Aviv (IL); Sharon Zlochiver, Tel-Aviv (IL); Muhammad Mahajna, Umm el Fahem (IL)

(73) Assignee: OsteoSee Ltd., Modiin Ilit (IL)

(*) Notice: Subject to any disclaimer, the term of this patent is extended or adjusted under 35 U.S.C. 154(b) by 398 days.

(21) Appl. No.: 14/893,109

(22) PCT Filed: May 26, 2014

(86) PCT No.: PCT/IL2014/050473
§ 371 (c)(1),
(2) Date: Nov. 23, 2015

(87) PCT Pub. No.: WO2014/191991
PCT Pub. Date: Dec. 4, 2014

(65) Prior Publication Data
US 2016/0100791 A1    Apr. 14, 2016

Related U.S. Application Data

(60) Provisional application No. 61/827,604, filed on May 26, 2013.

(51) Int. Cl.
*A61B 5/053* (2006.01)
*A61B 5/00* (2006.01)

(52) U.S. Cl.
CPC ............ *A61B 5/4509* (2013.01); *A61B 5/053* (2013.01); *A61B 5/0536* (2013.01); *A61B 5/6831* (2013.01)

(58) Field of Classification Search
CPC ..... A61B 5/4509; A61B 5/053; A61B 5/0536; A61B 5/6831
(Continued)

(56) References Cited

U.S. PATENT DOCUMENTS 5,782,763 A    7/1998   Bianco et al.
6,236,886 B1*  5/2001   Cherepenin .......... A61B 5/0536
                                                            600/547
(Continued)

FOREIGN PATENT DOCUMENTS

DE   102011118811   5/2013
EP   1530983        5/2005
(Continued)

OTHER PUBLICATIONS

International Preliminary Report on Patentability dated Dec. 10, 2015 From the International Bureau of WIPO Re. Application No. PCT/IL2014/050473.
(Continued)

*Primary Examiner* — Daniel L Cerioni

(57) ABSTRACT

A method of measuring Bone Mineral Density (BMD) including providing a model of a plurality of constituents of at least a portion of a subject body, the model including at least one bone constituent, injecting electric current into the portion of the subject body using a current injection electrode, such that at least part of the current flows through the at least one bone constituent, measuring a value of electric potential at a surface of the subject body using a pickup electrode, using a value of the injected electric current as input to a model of the at least a portion of a subject body, and calculating a value of conductance of the bone constituent corresponding to a value of the injected electric current and the measured value of the electric potential. Related apparatus and methods are also described.

18 Claims, 14 Drawing Sheets
(7 of 14 Drawing Sheet(s) Filed in Color)

(58) Field of Classification Search
USPC .......................................................... 600/547
See application file for complete search history.

(56) References Cited

U.S. PATENT DOCUMENTS

| | | | |
|---|---|---|---|
| 7,096,061 | B2 | 8/2006 | Arad |
| 7,534,419 | B2 | 5/2009 | Lewandrowski et al. |
| 7,847,565 | B2 | 12/2010 | Woo et al. |
| 7,907,998 | B2 | 3/2011 | Arad (Abboud) |
| 8,131,354 | B2 | 3/2012 | Arad (Abboud) |
| 2004/0054298 | A1 | 3/2004 | Masuo et al. |
| 2010/0198101 | A1 | 8/2010 | Song et al. |
| 2012/0150050 | A1 | 6/2012 | Arad (Abboud) |
| 2012/0271192 | A1 | 10/2012 | Just et al. |
| 2013/0085362 | A1 | 4/2013 | Choi et al. |
| 2013/0102870 | A1 | 4/2013 | Murakawa et al. |
| 2013/0131460 | A1* | 5/2013 | Yuen .................. A61B 5/04085 600/301 |
| 2013/0195325 | A1* | 8/2013 | Lang ................... G01B 15/045 382/128 |
| 2013/0211280 | A1* | 8/2013 | Gregory ................ A61B 5/053 600/547 |

FOREIGN PATENT DOCUMENTS

| | | |
|---|---|---|
| WO | WO 2004/110552 | 12/2004 |
| WO | WO 2007/089062 | 8/2007 |
| WO | WO 2008/064426 | 6/2008 |
| WO | WO 2014/191991 | 12/2014 |

OTHER PUBLICATIONS

International Search Report and the Written Opinion dated Oct. 19, 2014 From the International Searching Authority Re. Application No. PCT/IL2014/050473.
Arad et al. "Diagnosis of Elderly Pneumonia Patients Using a Parametric Electrical Impedance Tomography System—A Preliminary Study", International Journal Medical Engineering and Informatics, 2(4): 355-363, 2010.
Arad et al. "Estimating Pulmonary Congestion in Elderly Patients Using Bio-Impedance Technique: Correlation With Clinical Examination and X-Ray Results", Medical Engineering & Physics, 31: 959-963, 2009.
Arad et al. "The Detection of Pleural Effusion Using a Parametric EIT Technique", Physiological Measurement, 30: 421-428, 2009.
BeamMed "Sunlight—The Multi-Site Advantage", BeamMed, 2 P.
Freimark et al. "Monitoring Lung Fluid Content in CHF Patients Under Intravenous Diuretics Treatment Using Bio-Impedance Measurements", Physiological Measurement, 28: S269-S277, 2007.
Gabriel et al. "The Dielectric Properties of Biological Tissues: I. Literature Survey", Physics in Medicine and Biology, 41(11): 2231-2249, Nov. 1996.
Gabriel et al. "The Dielectric Properties of Biological Tissues: III. Parametric Models for the Dielectric Spectrum of Tissues", Physics in Medicine and Biology, 41(11): 2271-2293, Nov. 1996.
Horman et al. "Parametric EIT Vs. Intra-Thoracic Impedance for Monitoring Pulmonary Edema Using a Two Dimensional Theoretical Model of the Thorax", International Journal of Medical Engineering and Informatics, 5(2): 117-125, 2013.
Katz et al. "Induced Current Bio-Impedance Technique for Monitoring Bone Mineral Density—A Simulation Model", Annals of Biomedical Engineering, 34(8): 1332-1342, Aug. 2006.
Mhajna et al. "Assessment of Cardiac Stroke Volume in Patients With Implanted Cardiac Pacemaker Using Parametric Electrical Impedance Tomography: A Theoretical 2D Study", International Journal for Numerical Methods in Biomedical Engineering, 29: 630-640, Apr. 19, 2013.
Nunez "Electric Fields of the Brain. The Neurophysics of EEG", Oxford University Press, p. 66-71, 114-163, 458-465, 1981.
Radai et al. "A Novel Telemedicine System for Monitoring Congestive Heart Failure Patients", Congestive Heart Failure, 14: 239-244, 2008.
Shahidi et al. "Forward Problem of Electrocardiography: Construction of Human Torso Models and Field Calculations Using Finite Element Method", Medical & Biological Engineering & Computing, MBEC, 32(4 Suppl.): S25-S33, Jul. 1994.
Souza Cruz et al. "Bone Density Measuremnet Through Electromagnetic Waves", The 2013 Biomedical Engineering International Conference (BMEiCON-2013), 5 P., 2013.
Williams et al. "The Electrical and Dielectric Properties of Human Bone Tissue and Their Relationship With Density and Bone Mineral Content", Annals of Biomedical Engineering, 24: 222-223, 1996.
Zlochiver et al. "A Portable Bio-Impedance System for Monitoring Lung Resistivity", Medical Engineering & Physics, 29: 93-100, 2007.
Zlochiver et al. "Monitoring Lung Resistivity Changes in Congestive Heart Failure Patients Using the Bioimpedance Technique", Congestive Heart Failure, CHF, 11(6): 289-293, Nov.-Dec. 2005.
Zlochiver et al. "Parametric EIT for Monitoring Cardiac Stroke Volume", Physiological Measurement, 27: S139-S146, 2006.
Supplementary European Search Report and the European Search Opinion dated Dec. 19, 2016 From the European Patent Office Re. Application No. 14803750.0. (7 Pages).
Communication Pursuant to Article 94(3) EPC dated Jan. 31 2018 From the European Patent Office Re. Application No. 14803750.0 (4 Pages).
Communication Pursuant to Article 94(3) EPC dated Sep. 14, 2018 From the European Patent Office Re. Application No. 14803750.0. (5 Pages).

\* cited by examiner

DIAGNOSTIC AND MONITORING ELECTRICAL IMPEDANCE TOMOGRAPHY (EIT) SYSTEM FOR OSTEOPOROSIS

RELATED APPLICATIONS

This application is a National Phase of PCT Patent Application No. PCT/IL2014/050473 having International filing date of May 26, 2014, which claims the benefit of priority under 35 USC § 119(e) of U.S. Provisional Patent Application 61/827,604 filed May 26, 2013.

The contents of the above applications are all incorporated by reference as if fully set forth herein in their entirety.

FIELD AND BACKGROUND OF THE INVENTION

The present invention, in some embodiments thereof, relates to a system and method of injecting current into a body, measuring electric potential at a surface of the body, and using a model of the body to calculate bone dielectric properties for diagnosis and monitoring of Osteoporosis, and more particularly, but not exclusively, to using Electrical Impedance Tomography (EIT) for diagnosis and monitoring of Osteoporosis.

Osteoporosis is a disease in which density and quality of bones is reduced, leading to a weakness of the skeleton and to an increased risk of fracture, particularly of the spine, wrist and hip. Osteoporosis occurs when a body fails to form enough new bone. Osteoporosis and associated fractures are an important cause of mortality and morbidity. Osteoporosis is a global problem which is increasing in significance as the population of the world both grows and ages. Worldwide, lifetime risk for osteoporotic fractures in women is 30-50%. In men, the risk is 15-30%. There are three main types of Osteoporosis fractures: (1) Wrist fracture, (2) Vertebral fracture and (3) Hip fracture.

Since bone loss occurs without symptoms, there are no symptoms in the early stages of Osteoporosis and it's often called the "silent disease". In many cases the first symptom is a broken bone! Patients with Osteoporosis may not know that they have the disease until their bones become so weak that a sudden strain, bump, or fall causes a hip fracture or a vertebra to collapse. Collapsed vertebra may initially be felt or seen in the form of severe back pain, loss of height, or spinal deformities such as kyphosis, or a severely stooped posture.

Researchers estimate that about 1 out of 3 women over the age of 50 will suffer a fracture due to Osteoporosis. About half of all women over the age of 60 will have a fracture of the hip, wrist, or vertebra (bones of the spine). Once a woman suffers a first vertebral fracture, there is a five-fold increase in the risk of developing a new fracture within one year.

Approximately, 1.6 million hip fractures occur each year worldwide. The highest risk of hip fractures is seen in Norway, Sweden, Iceland, Denmark and the USA. Currently, there is an increasing incidence of hip fractures in developed cities in Asia. 1 out of 4 hip fractures occur in Asia and Latin America. In the Middle East, the burden of Osteoporosis in the general population is expected to increase and is becoming a heavy financial burden.

According to WHO, Osteoporosis is second only to cardiovascular disease as a global healthcare problem and medical studies show a 50-year-old woman has a similar lifetime risk of dying from hip fracture as from breast cancer. Since Osteoporosis affects the elderly population which is growing, it will put a bigger burden to the healthcare system, as treatment of Osteoporosis is expensive. Unless swift action is taken, Osteoporosis can escalate into an economic threat. The International Osteoporosis Foundation (IOF) estimates that the annual direct cost of treating Osteoporosis fractures of people in the workplace in the USA, Canada and Europe alone is approximately 48 billion USD. The worldwide cost burden of Osteoporosis (for all ages) is forecast to increase to 131.5 billion USD by 2050. Osteoporosis also results in huge indirect costs that are rarely calculated and which are probably at least 20% of the direct costs.

The annual incidence rate of osteoporotic fractures in women is greater than the combined incidence rates of heart attack, stroke and breast cancer.

An article titled "Induced Current Bio-impedance Technique for Monitoring Bone Mineral Density—A Simulation Model", by Sagie Katz, Sharon Zlochiver, and Shimon Abboud (the present inventor) published in Annals of Biomedical Engineering, Vol. 34, No. 8, August 2006, pp. 1332-1342, describes a feasibility study of using an induced current bio-impedance technique as a method to determine and monitor bone mineral density (BMD). BMD was theoretically evaluated using a computerized simulation model. A 2D polar coordinate numerical solver was developed using the Finite Volume Method (FVM) in order to simulate developed potentials over an axial CT cross section of a human thigh. Varying femur BMDs were simulated by varying femur relative permittivity values. At a chosen excitation current of 1 ampere at a frequency of 20 kHz, the real component of the surface potential was found to be more sensitive to BMD variation than the imaginary component (3.9 µVg-1 cm3 compared with 0.174 µVg-1 cm3).

A correlation between varying femur permittivity values and a real component of a developed surface potential was found to be quadratic, and influenced by coil geometry and measuring point location. Measurement sensitivity was improved either by taking the measuring point to be closer to the femur location or by minimizing the distance between the excitation coil and the femur.

Additional background art relating to measurement of volume of chest organs using EIT includes:
U.S. Published patent application number 2012/0150050 of Arad;
U.S. Pat. No. 8,131,354 of Arad;
U.S. Pat. No. 7,907,998 of Arad; and
U.S. Pat. No. 7,096,061 of Arad.

Additional background art includes:
An article titled "The dielectric properties of biological tissues: I. Literature Survey", by C. Gabriel, S. Gabriely and E. Corthout, published in Phys. Med. Biol. 41 (1996) 2231-2249.
An article titled "Parametric EIT vs. intra-thoracic impedance for monitoring pulmonary edema using a two dimensional theoretical model of the thorax" by Keren Horman and Shimon Abboud, published in Int. J. Medical Engineering and Informatics, Vol. 5, No. 2, 2013.
An article titled "Assessment of cardiac stroke volume in patients with implanted cardiac pacemaker using parametric electrical impedance tomography: A theoretical 2D study" by Muhammad Mhajna and Shimon Abboud, published in International Journal For Numerical Methods In Biomedical Engineering 2013; 29:630-640, and also published online 19 Apr. 2013 in Wiley Online Library (wileyonlinelibrary(dot)com). DOI: 10.1002/cnm.2550.

A white paper by titled "Sunlight—The Multi-Site Advantage", by a company named BeamMed Ltd., of 8 Ha-Lapid St., P.O Box 7520, Petah Tikva 49170, Israel, which describes a multi-site bone sonometer (ultrasound bone density measurement system).

An article titled "Monitoring lung fluid content in CHF patients under intravenous diuretics treatment using bio-impedance measurements" by D Freimark, M Arad, R Sokolover, S Zlochiver and S Abboud, in Physiol. Meas. 28 (2007) S269-S277 doi:10.1088/0967-3334/28/7/S20.

An article titled "Monitoring Lung Resistivity Changes in Congestive Heart Failure Patients Using the Bioimpedance technique", by Sharon Zlochiver, Michal M. Radai, Deganit Barak-Shinar, Tuvia Ben-Gal, Vicky Yaari, Boris Strasberg, and Shimon Abboud, published in Congestive Heart Failure® November December 2005.

An article titled "A portable bio-impedance system for monitoring lung resistivity" by S. Zlochiver, M. Arad, M. M. Radai, D. Barak-Shinar, H. Krief, T. Engelman, R. Ben-Yehuda, A. Adunsky and S. Abboud, in Medical Engineering & Physics 29 (2007) 93-100.

An article titled "The detection of pleural effusion using a parametric EIT technique" by M Arad, S Zlochiver, T Davidson, Y Shoenfeld, A Adunsky and S Abboud, in Physiol. Meas. 30 (2009) 421-428.

An article titled "A Novel Telemedicine System for Monitoring Congestive Heart Failure Patients", by Michal M Radai, Marina Arad, Sharon Zlochiver, Haim Krief, Tzvika Engelman and Shimon Abboud, in telemedicine for CHF patients, September October 2008.

An article titled "Estimating pulmonary congestion in elderly patients using bio-impedance technique: Correlation with clinical examination and X-ray results" by Marina Arad, Sharon Zlochiver, Tina Davidson, Ora Shovman, Yehuda Shoenfeld, Avraham Adunsky and Shimon Abboud, in Medical Engineering & Physics 31 (2009) 959-963.

An article titled "Parametric EIT for monitoring cardiac stroke volume" by S Zlochiver, D Freimark, M Arad, A Adunsky and S Abboud, in Physiol. Meas. 27 (2006) S139-S146.

An article titled "Diagnosis of elderly pneumonia patients using a parametric electrical impedance tomography system—a preliminary study" by M. Arad, A. Adunsky, S. Zlochiver, S. Abboud and T. Davidson, in Int. J. Medical Engineering and Informatics, Vol. 2, No. 4, 2010.

An article titled "The Electrical and Dielectric Properties of Human Bone Tissue and Their Relationship with Density and Bone Mineral Content" by Paul Allen Williams and Subrata Saha, published in Annals of Biomedical Engineering, Vol. 24, pp. 222-233, 1996.

The disclosures of all references mentioned above and throughout the present specification, as well as the disclosures of all references mentioned in those references, are hereby incorporated herein by reference.

SUMMARY OF THE INVENTION

In some embodiments of the invention, alternating current is injected into a body, or a portion of the body, the current being injected into the body by one or more injection electrodes touching the body surface and making electrical contact with the body surface, and electric potential is measured at the body surface using one or more pickup electrodes touching the body surface and making electrical contact with the body surface.

In some embodiments a model of the body, or the portion of the body, and its main constituents, including initial values for conductivity of the main constituents, is used when calculating conductivity of the bone constituent.

The term "conductivity" in all its grammatical forms is used throughout the present specification and claims to stand for "complex conductivity" which may include both conductivity and permittivity, as will be recognized by a person skilled in the art.

In some embodiments the value of current being injected into the body and electric potential measured at the body surface are entered into the model, and conductivity of the bone constituent of the model is adjusted to fit the injected current and measured potential.

In some embodiments the adjustment of the conductivity of the bone constituent of the model is made so as to minimize differences between measured electric current and/or electric potential and modeled electric current and/or electric potential.

In some embodiments, one or more of the injection electrodes which inject the current are also used as pickup electrodes to measure the potential.

In some embodiments, active electrodes are used. A potential problem of using normal electrodes is skin preparation. Home users typically won't prepare the skin. An active electrode is an electrode which requires no skin preparation, and is potentially also robust to noises, and has good sensitivity. Passive electrodes are cheap and easy to manufacture. However, passive electrodes require skin preparation in the spot under electrode, and special pastes are also required to lower impedance between electrodes and skin. Those requirements are usually acceptable, but not always welcome. An active electrode is an electrode that requires no skin preparation. In some embodiments, the active electrode includes a preamplifier placed very close to the skin, optionally inside the electrode. Dry skin impedance can potentially be omitted by using an amplifier with high input impedance. Another reason to use active electrodes can be safety. Because dry skin-electrode impedance is high, for example a few megohms, then the isolation barrier is high. Using active electrodes a chance for an electrocution is much smaller comparing to passive electrodes.

A potential advantage of using one or more electrodes to inject current rather than a coil to induce current is control over the location of injection electrodes, relative to a subject's body and relative to pickup electrodes, over induced current which uses a coil with a less-defined location relative to a subject's body and to the pickup electrodes.

The injected current and the measured potential are used to calculate bone mineral density (BMD) by using Electrical Impedance Tomography (EIT).

In some embodiments, parametric EIT is used to calculate bone mineral density, as further described below.

There are systems which inject current into a body and measure resistance, and purport to estimate BMD based on the measured path resistance (Ohm's law). Such measurements are considered inaccurate for various reasons, including that the resistance is dependent on the path which the electric current takes between injector and pickup; and that measuring path resistance does not model an actual shape of a body well.

Some embodiments of the invention use a more elaborate model of the body, or section of a body, which is being measured. Measuring BMD optionally starts with an initial model of a body, optionally divided into several portions, or constituents, including one or more of: bone, muscle, fat, skin and so on. Each one of the portions optionally includes an initial shape, and/or an initial value of conductance for each one of the portions.

In some embodiments, the model of the body is a three dimensional model.

In some embodiments, the geometry of a model corresponds to a body section being measured. By way of a non-limiting example, when a thigh bone is being measured, the model may be a model of a single generally cylindrical bone, surrounded by non-bone tissue also in a generally cylindrical shape. Measurements of other bones and body portions may include other models. Some examples include:

a leg may include two generally cylindrical bones surrounded by tissue;

a cortical bone, or similar locations, may include a model of a bone with two or more portions, each of the portions having possibly different conductivity;

a wrist may include a model of bones in the vicinity of the wrist, and the electrode may be placed in a circle about the wrist; and a spinal cord, where the model includes a torus shape for a bone, or a vertebra shape for a bone. In the case of the spinal cord the electrodes may optionally be arranged as a ring around one vertebra or as an array.

In some embodiments the voxel size in the model is 0.5, 1, 3, 5 or even 10 millimeters on a side.

In some embodiments the voxel size in the model is 3 cubic millimeters.

Voxel size optionally depends on a bone being measured. For example, for a finger bone a smaller voxel size may optionally be used, for example a voxel size of 1 cubic millimeter, while for a thigh bone a larger voxel size may optionally be used, for example a voxel size of 1 cubic centimeter, or even more.

In some embodiments, the model of the body portion comprises a non-Cartesian grid, in which grid lines optionally approximately correspond to a shape of the portion of the subject body on which measurement is being performed. Such a non-Cartesian grid can potentially minimize errors due to misfit between a physical and a computational shape of a boundary of a tissue or organ.

In some embodiments the model and BMD calculation include an iterative improvement of the model, as described further below.

In some embodiments, the initial shape corresponds to an average shape for a body based on, for example, gender, and height and/or weight.

In some embodiments, the initial shape corresponds to measurement actually made on a patient's body—the measurements optionally made, by way of some non-limiting examples, by measuring length of limbs, circumference of a head, and/or actual measurements using various imaging modalities such as X-ray, CT, MRI, and so on, optionally using existing imagery of the patient's body.

In some embodiments, in case of a second measurement of a same patient, the initial shape corresponds to the model used for the patient in a prior measurement. Such an initial condition for measurement is potentially useful since in many cases a patient's bone dimensions vary little over a time between BMD measurement and tracking.

In some embodiments, the initial conductance values of the portions correspond to an average shape for a body based on, for example, gender, and height and/or weight.

In some embodiments, the initial conductance values correspond to measurements actually made on a patient's body—the measurements optionally made, by way of some non-limiting examples, by making such measurements during surgery, such as during open orthopedic surgery like bone grafting, or during total hip replacement, as also mentioned below.

In some embodiments, in case of a second measurement of a same patient, the initial conductance values correspond to the model used for the patient in a prior measurement.

In some embodiments, two injection electrodes are used, and two pickup electrodes are used, for a relatively compact configuration.

In some embodiments, a system built for measuring BMD is compact enough for use in a home setting, whether performing measurements and recording data for analysis at some medical setting, or for analysis by the home system.

In some embodiments, a sleeve is provided for sliding over a patient's body and placing the electrodes in a defined geometric relation to each other. The sleeve may include the electrodes and conductors connected to the electrodes, or the sleeve may include holes placed for guiding the location of the electrodes. The sleeve may have instructions printed upon it, guiding which electrode goes where, and/or how to orient the sleeve upon a patient's body. Example embodiments of such a sleeve include: a sleeve for a thigh, a sleeve for a leg, a sleeve for an ankle, a sleeve for a foot, a sleeve for an arm, and so on.

In some embodiments the sleeve includes specific attachment appendages, appropriate for a specific body part for which the sleeve is intended.

In some embodiments, different sleeves correspond to different body parts and different electrode locations, and a calculation program used for estimating BMD optionally includes preset values corresponding to preset geometries of sleeves and/or electrode locations and physical properties such as permittivity of specific body parts.

In some embodiments, electrode area is on an order of 2 square centimeters per electrode, although electrode area from 0.1 square centimeters to 10 square centimeters may also be used. Electrode area optionally depends on available area. For example, a finger supports smaller electrodes than a thigh.

An estimate of loss of bone mass can be made by a physician through a bone mineral density test (BMD). A typical BMD test uses ionizing radiation, it should not be used on a patient on a routine basis and it is not practical outside a hospital, in a community setting. One goal of some embodiments of the invention is to improve diagnostics and monitoring of osteoporosis in hospitals and clinics by providing a simple, sensitive and accurate measurement of bone mineral density that can be used on a patient on a routine basis.

Some embodiments of the invention include a technique which enables detecting low bone density before a fracture occurs. The technique can confirm a diagnosis of osteoporosis if the patient has already fractured a bone. The technique can also predict a probability of fracturing a bone in the future. The technique can also enable determination of a rate of bone loss and/or monitor the effects of treatment if measurements are conducted at intervals, such as intervals of a month, a year, or more.

Electrical Impedance Tomography (EIT) is a method that provides information of the spatial electrical conductivity distribution within the human body. The method is based on applying small magnitude alternating electric currents to the body and measuring developing electric potentials on the surface of the body. The large variation of tissues' electric and dielectric properties makes EIT a possible technique for body monitoring and imaging. Some limitations of the technique are its high sensitivity to electrical and geometrical measurement noises and its need for large computational resources and hence the technique is not practiced at clinics.

One way to overcome the above limitations is to use a parametric reconstruction scheme. A parametric Electrical Impedance Tomography (pEIT) algorithm was developed in the Department of Biomedical Engineering of Tel Aviv University for measuring pulmonary edema and cardiac output in Congestive Heart Failure patients.

In parametric EIT one does not reconstruct the entire spatial conductivity distribution as in regular EIT. Instead, the values of finite number of parameters which can be used to describe the geometrical configuration of the organ of interest are reconstructed.

The pEIT method is a variation of EIT which may be more efficient for a clinical setup. For example, the pEIT method potentially requires fewer injection and/or pickup electrodes.

With EIT reconstruction, a 3D model, or a 2D image, is divided to pixels. Using the pEIT method, the model and/or image is divided to functional areas—typically divided to specific organs and/or tissues known to potentially differ in electric parameters such as conductance. All cells in an organ/tissue are optionally assumed, at least initially, to have a same average conductivity. Using the pEIT method, the number of independent measurements required can potentially be as low as the number of organs in the model rather than the number of pixels in the model.

The pEIT algorithm was developed to perform fast and be less sensitive to measurement noises. In some embodiments, instead of reconstructing a full tomographic image of a body, the pEIT algorithm reconstructs only a small number of parameters which can be used to model anatomical or physiological phenomena.

One application of the pEIT technique is to evaluate bone mineral density (BMD), as frequently required during Osteoporosis tracking. In studies made on bones taken from both humans and animals, a strong linear correlation between relative permittivity (and thus impedivity) of bone tissue and many of its mechanical characteristics, especially the BMD, was found. Knowing bone dielectric properties is helpful to predict bone quality and strength.

BMD measurement is the main tool for Osteoporosis prevention, diagnosis and management. In 1993, the World Health Organization (WHO) proposed criteria for the diagnosis of Osteoporosis based on BMD measurement results. These criteria take advantage of the fact that fracture risk increases with decreasing BMD.

According to an aspect of some embodiments of the present invention there is provided a method of measuring Bone Mineral Density (BMD) including providing a model of a plurality of constituents of at least a portion of a subject body, the model including at least one bone constituent, injecting electric current into the portion of the subject body using a current injection electrode, such that at least part of the current flows through the at least one bone constituent, measuring a value of electric potential at a surface of the subject body using a pickup electrode, using a value of the injected electric current as input to a model of the at least a portion of a subject body, and calculating a value of conductance of the bone constituent corresponding to a value of the injected electric current and the measured value of the electric potential.

According to some embodiments of the invention, the model includes an Electrical Impedance Tomography (EIT) model. According to some embodiments of the invention, the EIT model is a parametric EIT (pEIT) model.

According to some embodiments of the invention, the injecting electric current into the portion of the subject body is performed at just one location in the subject body. According to some embodiments of the invention, the injecting electric current into the portion of the subject body is performed at just two locations in the subject body. According to some embodiments of the invention, the measuring a value of electric potential at a surface of the subject body is performed at just two locations at the surface of the subject body.

According to some embodiments of the invention, further including calculating Bone Mineral Density (BMD) of the bone constituent based, at least in part, on the value of conductance of the bone constituent.

According to some embodiments of the invention, the calculating a value of conductance of the bone constituent includes:
(a) providing an initial bone conductivity value for use as a bone conductivity value for bone being measured,
(b) generating a conductivity distribution model including the bone conductivity value and including non-bone tissue conductivity,
(c) forward calculating a value of electric potential at the pickup electrode,
(d) minimizing a difference between the value calculated according to step (c) and the value of electric potential measured at the pickup electrode by adjusting the bone conductivity value, and
(e) calculating a value of conductance of the bone constituent based on the adjusted bone conductivity value.

According to some embodiments of the invention, the injecting electric current into the body using a current injection electrode includes injecting electric current into the body using a plurality of current injection electrodes. According to some embodiments of the invention, the plurality of current injection electrodes includes two injection electrodes.

According to some embodiments of the invention, the measuring a value of electric potential at a surface of the body using a pickup electrode includes measuring a plurality of values of electric potential at the surface of the body using a plurality of pickup electrodes.

According to some embodiments of the invention, the bone constituent includes a long bone.

According to some embodiments of the invention, the plurality of current injection electrodes are arranged in a line along the bone constituent. According to some embodiments of the invention, the plurality of current injection electrodes are arranged in an array adjacent to the bone constituent. According to some embodiments of the invention, the plurality of current injection electrodes are arranged in a ring adjacent to the bone constituent.

According to some embodiments of the invention, the plurality of pickup electrodes are arranged in a line along the bone constituent. According to some embodiments of the invention, the plurality of pickup electrodes are arranged in an array adjacent to the bone constituent. According to some embodiments of the invention, the plurality of pickup electrodes are arranged in a ring adjacent to the bone constituent.

According to some embodiments of the invention, the value calculated in (c) includes a vector including a plurality of values calculated according to (c), the value of the electric potential measured includes a vector including a plurality of values of electric potential measured at a plurality of pickup electrodes, and the minimizing a difference between the value calculated in (c) and the value of electric potential measured at the pickup electrode by adjusting the bone conductivity value includes minimizing a squared difference between the vector including a plurality of values calculated according to (c) and the vector including a plurality of values of electric potential measured at the plurality of pickup electrodes by adjusting the bone conductivity value.

According to some embodiments the minimizing a difference between the value calculated in (c) and the value of electric potential measured at the pickup electrode by adjusting the bone conductivity value optionally includes minimizing a difference in a norm of complex values.

According to some embodiments of the invention, the calculating bone conductivity value is an iterative calculation including repeating (b) to (d) a plurality of times.

According to some embodiments of the invention, the iterative calculation includes a Levenberg-Marquardt parametric optimization scheme.

According to some embodiments of the invention, the iterative calculation includes a Tikhonov regularization scheme.

According to some embodiments of the invention, the EIT model includes a grid having a non-cubic shape corresponding to a shape of the portion of the subject body on which measurement is being performed.

According to some embodiments of the invention, the EIT model includes a non-Cartesian grid in which grid lines approximately correspond to a shape of the portion of the subject body on which measurement is being performed.

According to some embodiments of the invention, the EIT model includes a non-Cartesian grid in which grid lines approximately correspond to a shape of the bone constituent of the portion of the subject body on which measurement is being performed.

According to some embodiments of the invention, the injected electric current is alternating current. According to some embodiments of the invention, the injected electric current is alternating current at a frequency in the order of 100 kHz.

According to some embodiments of the invention, the value of the measured electric potential is a value of a real component of the measured electric potential.

According to some embodiments of the invention, the injected alternating current is at a frequency of 20 KHz. According to some embodiments of the invention, the injecting electric current includes injecting current in a range of 1-10 milliamperes.

According to some embodiments of the invention, further including performing a plurality of BMD measurements and determining a rate of BMD loss over time.

According to an aspect of some embodiments of the present invention there is provided a system for measuring Bone Mineral Density (BMD) including a computational unit which includes a model of a plurality of constituents of at least a portion of a subject, the model including at least one bone constituent, an injection electrode for injecting electric current into the portion of the subject, such that at least part of the current flows through the at least one bone constituent, a pickup electrode for measuring a value of electric potential at a surface of the subject, wherein the computational unit receives input of what value of the injected electric current is injected into the portion of the subject, receives input of a measured value of electric potential at the surface of the subject, uses the value of the injected electric current as input to the model, and calculates a value of conductance of the bone constituent corresponding to the value of the injected electric current and the measured value of the electric potential.

According to some embodiments of the invention, the model includes an Electrical Impedance Tomography (EIT) model. According to some embodiments of the invention, the EIT model is a parametric EIT (pEIT) model.

According to some embodiments of the invention, at least one electrode is an active electrode.

According to some embodiments of the invention, including exactly one injection electrode. According to some embodiments of the invention, including a plurality of injection electrodes. According to some embodiments of the invention, including exactly two injection electrodes.

According to some embodiments of the invention, including exactly one pickup electrode. According to some embodiments of the invention, including a plurality of pickup electrodes. According to some embodiments of the invention, including exactly two pickup electrodes.

According to some embodiments of the invention, further including a sleeve for sliding over a subject and placing at least some of the electrodes in a defined geometric relation to each other. According to some embodiments of the invention, at least some of the electrodes are arranged in a line. According to some embodiments of the invention, at least some of the electrodes are arranged as an array. According to some embodiments of the invention, at least some of the electrodes are arranged as a ring.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a simplified illustration of a full 3D phantom model used in computerized simulations according to an example embodiment of the invention;

FIG. 1B is a simplified illustration of a cross section of the thigh of the phantom of FIG. 1A, along with positions of electrodes used in the simulations and in the potential measurements;

FIG. 2 is a graph depicting the results of computer simulations of an example embodiment of the invention;

FIG. 3 is a simplified illustration of an example embodiment of the invention;

FIG. 4 is a simplified flow chart illustration of a method of measuring bone conductance according to an example embodiment of the invention;

FIGS. 5A and 5B are a top view cross section and a side view cross section respectively of a phantom according to an example embodiment of the invention;

FIG. 5C is a top view cross section of the phantom of FIGS. 5A and 5B;

FIGS. 6A and 6B are graphs describing error convergence of the SOR method in an example embodiment of the invention;

FIGS. 7A and 7B are potential maps showing a real part of a potential and an imaginary part of a potential simulated in the example embodiment of FIGS. 6A and 6B;

FIGS. 8A and 8B are graphs showing a real part of a potential and an imaginary part of a potential simulated in an example embodiment of the invention;

FIGS. 9A and 9B are graphs showing a real part of a potential delta and an imaginary part of a potential delta in comparisons of healthy bone to osteoporotic bone simulated in an example embodiment of the invention;

Figure 10:
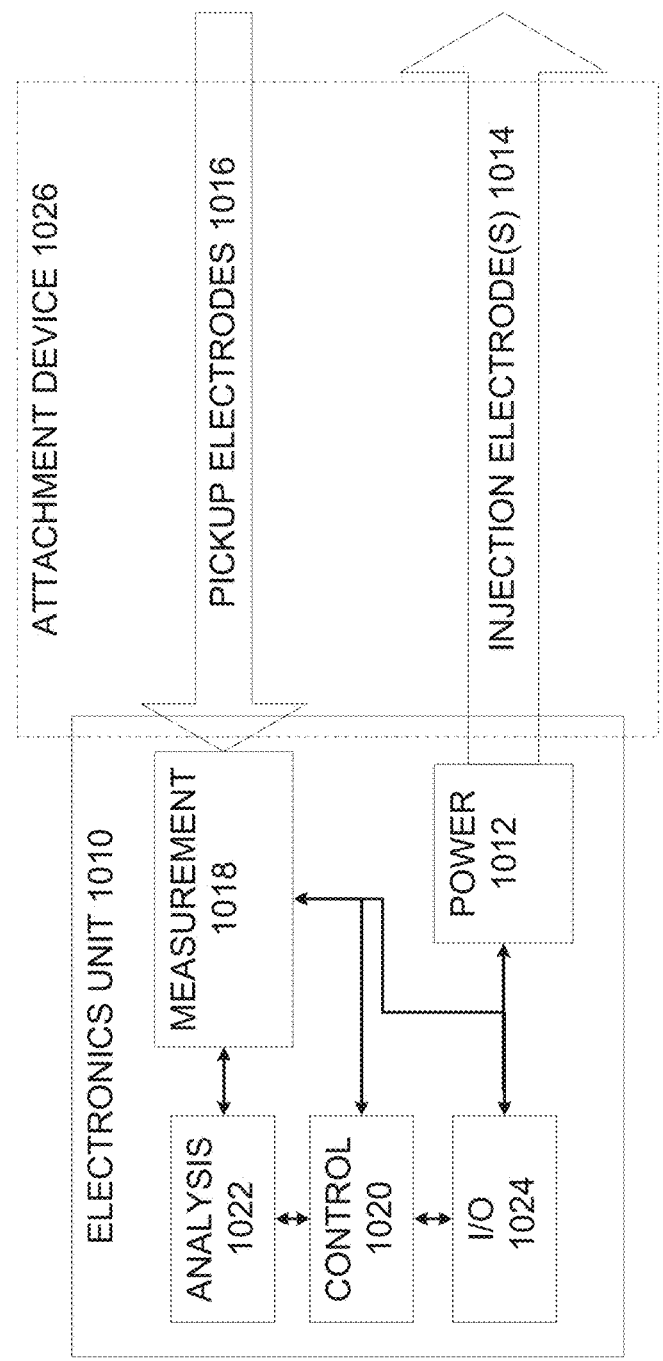
Figure 11A:
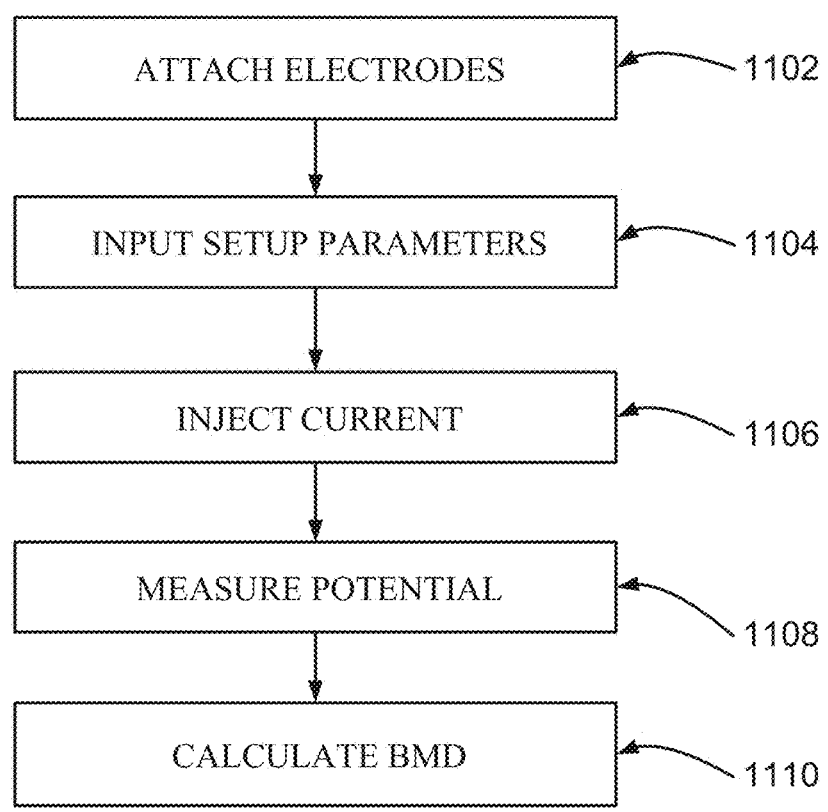
Figure 11B:
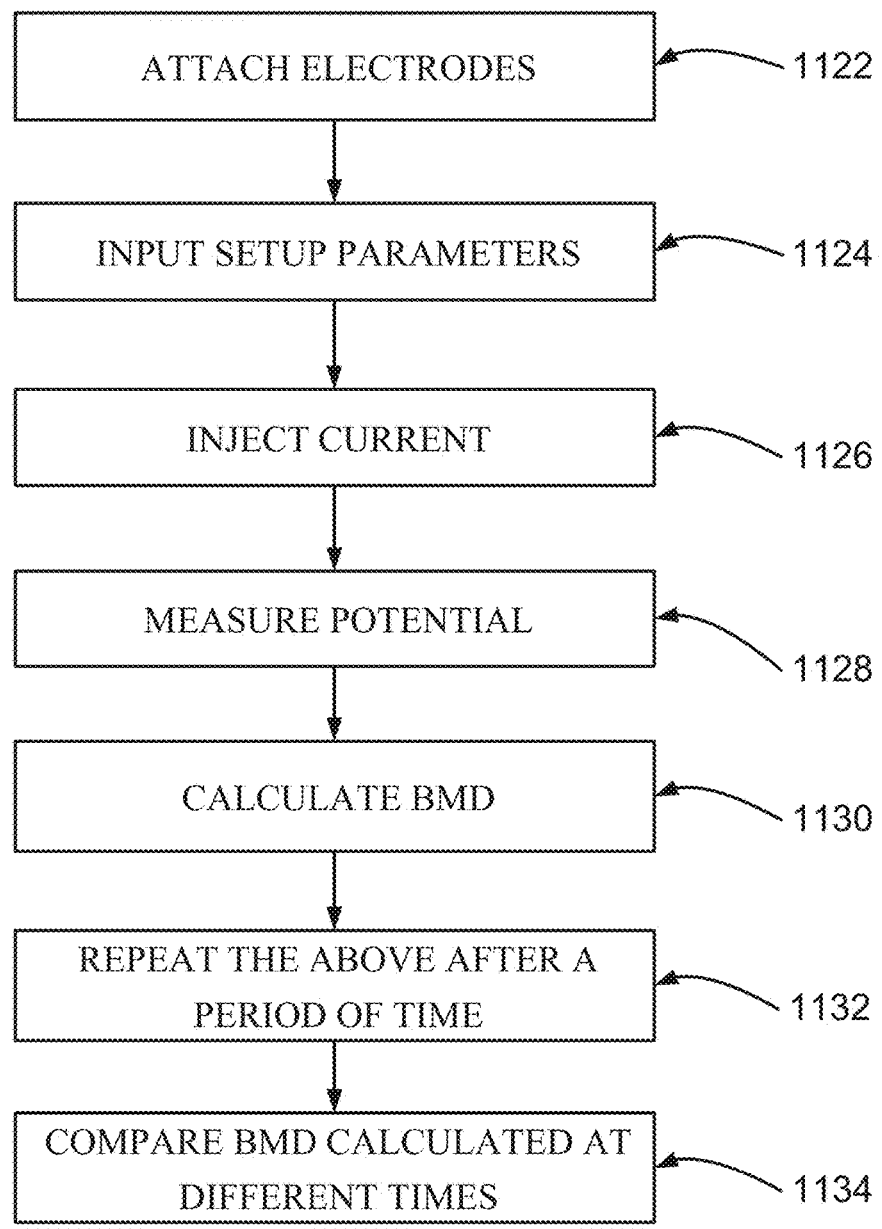

FIG. 10 is simplified block diagram of an example embodiment of the invention; and FIGS. 11A and 11B are simplified flow chart illustrations of example embodiments of the invention.

DESCRIPTION OF SPECIFIC EMBODIMENTS OF THE INVENTION

The present invention, in some embodiments thereof, relates to a system and method of injecting current into a body, measuring electric potential at a surface of the body, and using a model of the body to calculate bone dielectric properties for diagnosis and monitoring of Osteoporosis, and more particularly, but not exclusively, to using Electrical Impedance Tomography (EIT) for diagnosis and monitoring of Osteoporosis.

An article by the present inventor, mentioned above, describes using induced current in a body to measure Bone Mineral Density (BMD). Induced current in a body is typically produced by placing an electric coil near the body, and causing induced current by running alternating current through the coil. Surface potential is typically measured by electrodes touching the body surface and making electrical contact with the body surface.

In an injected current EIT system, low frequency sinusoidal currents are applied to a surface of a body by electrodes. In induced current Electrical Impedance Tomography, induction coils, encircling the body, are arranged at different positions. Time-varying magnetic fields are applied via the coils to induce electrical current in the conductive body. The developed electrical potentials are measured using sensor electrodes touching and optionally attached to the surface of the body.

An induced current bio-impedance technique was proposed in recent studies as an alternative method for applying current in volume conductors while avoiding direct contact with a patient's skin. On the face of it, while apparently attractive, the induced current technique may have one or more of the following limitations which may render the technique inferior to the injected current technique:

1. Induced current devices are typically more complicated than injected current devices. The induced current devices require positioning a subject in the midst of a magnetic field formed by surrounding coils, so a large apparatus is needed, which is typically positioned in hospital or clinical center environs. Home devices are more likely to be practicable using an injected current technique.

2. Correct, repetitive alignment of a patient relative to induction coils can be problematic, and inter-measurement errors are expected to be large. As the bio-impedance technique is sensitive to measurement noises, aligning measures are likely to be costly and sophisticated, presenting a problem in realizing such a system.

3. Sensitivity of the induced current technique to changes of tissue impedance, such as bone mineral density, is small, and absolute voltage measurements due to the typical induced currents are in the order of micro-volts, suggesting a low Signal to Noise Ratio (SNR).

4. Patient movement during a measurement potentially result in large errors, since a relative position between the patient and the induction coils changes. In an injected current scheme, the patients and the system potentially "move together" during measurement.

5. To enable induced current magnitudes strong enough to enable sufficient SNR, the induction coils should be driven with strong currents, which can potentially impose safety and power supply issues.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Currently, there are several non-invasive diagnostic techniques for bone quality evaluation such as Dual-Energy X-ray Absorptiometry (DEXA), Quantitative Computed Tomography (QCT) and ultrasound.

An example embodiment of the invention—the pEIT technique, proposes an alternative to those techniques; it is inexpensive relative to the existing techniques and it does not use ionizing radiation, thus it is well suited for long-term tracking which is often required in this field, particularly during Osteoporosis management, which may last over years, and include many repeat measurements. Moreover, the pEIT technique is optionally implemented in simple hardware, thus the pEIT technique can be applied in small clinics and even at home. In addition, in some situations, such as during open orthopedic surgery like bone grafting, or during total hip replacement, none of the existing techniques that give a direct measurement of bone quality can be applied. The pEIT technique, on the other hand, can be applied.

One example way of calculating a potential distribution for a given conductivity map and current injection is termed the Forward Problem, which is described mathematically by the volume conductor equation or Poisson's equation. Analytical solutions for Poisson's equation exist for a few simple geometries, beyond which a numerical method is optionally employed for solving physical equations which relate developing electrical potentials to injected current sources using realistic body geometry.

Many numerical methods can be used for bio-impedance simulations. One such method is the finite element method (FEM), but there are other methods which can be used, such as the finite volume method (FVM). Numerical solvers based on either FEM or FVM have been found to show good accuracy compared to an analytical solution when activated over validation models. The FVM solves the integral formulation of the governing Poisson's equation, and is potentially appropriate for flow-conservation systems, as in the case of some embodiments of the invention. Zero-flux boundary conditions are optionally fulfilled, and conductivity discontinuities at a boundary between different tissue types typically do not impose singularities for gradient calculations, as in differential numerical methods.

Embodiments of the invention are potentially flexible regarding mesh structures, and allow an easy introduction of anisotropy. A grid which is optionally used in the numerical solver can optionally vary according to the shape of the organ on which measurements are performed. For example, the thigh has a cylindrical shape, so a preferred grid of a thigh is optionally a cylindrical grid or an elliptic grid.

In some embodiments, a body part is entered into a calculation program, which selects a corresponding anisotropic model.

In some embodiments, a medical image or even a 3D imaging study of a body part, such as, by way of a non-limiting example, an X-ray image or a CT imaging study, is entered into a calculation program, which selects a corresponding anisotropic model.

In the Inverse Problem a conductivity map is reconstructed based on a set of the measured potentials.

An example embodiment which includes the pEIT system and method optionally reconstructs conductivity of a bone, which, as mentioned, is related to BMD.

In order to estimate the conductivity of the bones, Levenberg-Marquardt parametric optimization scheme is optionally utilized. Since the Levenberg-Marquardt parametric optimization scheme is an iterative method, the method involves (1) guessing initial conductivity, (2) generating a conductivity distribution consisting of all the original tissues and a constant conductivity in the bones region and (3) calculating the electrodes' potential using the forward solver. A 'true', that is a measured, potential is optionally measured using a set of electrodes. Then, two potential difference vectors ('true' & calculated) are obtained. The two potential vectors are then compared, optionally using Euclidian distance, and an initial guess of conductivity is iteratively updated, yielding a reduction in the error energy:

$$E = \|\Phi_{measured} - \Phi_{calculated}\|^2 \qquad \text{Equation 1}$$

The above process is optionally repeated, potentially bringing the Euclidian distance of Equation 1 to a local minimum.

Updating the conductivity distribution map is optionally performed by using the relation:

$$d_{k+1} = d_k - [\mathcal{J}_k^T \mathcal{J}_k + \lambda \cdot \text{diag}(\mathcal{J}_k^T \mathcal{J}_k)]^{-1} * \mathcal{J}_k^T [\varphi_c(\sigma_k) - \varphi_m] \qquad \text{Equation 2}$$

where $d_k$ is the conductivity of the bones. $\phi_c(d_k)$ is a calculated electrode potential difference vector for a k-th conductivity distribution, $\phi_m$ is a 'real' value of the electrode potential difference vector, $\lambda$ is a damping factor and $\text{diag}(\mathcal{J}_k^T \mathcal{J}_k)$ is the diagonal of the Hessian matrix. The k-th Jacobian matrix, $\mathcal{J}_k(d_k)$, is defined as:

$$\mathcal{J}_k(d_k) = \frac{\partial \phi_c(d_k)}{\partial d_k} \qquad \text{Equation 3}$$

In some embodiments, when there is one parameter to reconstruct, such as bone conductivity, bone permittivity, bone radius, location of center of bone, a Look Up Table (LUT) is optionally used for the estimation of the one parameter based on the measured potentials.

In some embodiments at least two or three parameters of the above-mentioned list of parameters are estimated, optionally using the above-mentioned parametric optimization scheme.

Tissues have a frequency dependent conductivity. Changes in bone permittivity, for example at a frequency of 100 kHz, strongly influence the real component of the surface potential. There is a good correlation between BMD variation and the real component of the surface potential. Reconstructed conductivity of the bones, which is directly related to the surface potentials, is correlated to the true conductivity values or the BMD.

In some embodiments of the invention the injected electric current is in a range of 1-10 milliamperes.

Embodiments using the pEIT technique potentially enable some major advantages over other known bone densitometry techniques such as Dual-Energy X-ray Absorptiometry (DEXA) or Quantitative Computed Tomography (QCT): (1) the pEIT technique is inexpensive to implement, (2) the pEIT technique does not use ionizing radiation and (3) the pEIT technique is appropriate for long-term and home monitoring. The pEIT technique provides a parameter (conductivity) which is related directly to the bone mineral density. In contrast to other techniques, where the relation between the investigated parameter and the BMD isn't well defined. Conductivity of a bone is not a patient-related parameter, making it easier to find a generalized relation between conductivity of a bone and BMD.

Some embodiments using the pEIT technique use a model defined by geometric parameters (measures of shape) and physiological parameters (measures of electrical conductance). In some embodiments parameter fitting is optionally performed.

In some embodiments, some simplifications are optionally used in creating a computerized model of the body which is used for the potential calculations. A model of a body or of a section of a body is optionally produced using other imaging modalities. Each tissue type (skin, fat, muscle, bone and bone marrow) is optionally considered to be homogenous; such that each complex conductivity value optionally represents a mean value of a tissue bulk.

In some embodiments, the model optionally excludes some small tissues. For example, in a thigh model, blood vessels (which may have some influence on the electrical field pattern due to high blood conductivity) are optionally discarded and/or ignored, due to their small size. Additionally, the tissues in some simplified models are optionally assumed to be isotropic, although this assumption may not be satisfied in some cases, especially concerning bone tissue.

It is noted that that no clear correlation between the relative permittivity and density for a purely cortical bone was found to date. In some embodiments of the invention, a permittivity to density relationship for cortical bone is optionally based on a combination of cortical bone and cancellous, spongy, bone.

In above-mentioned articles "Parametric EIT vs. intrathoracic impedance for monitoring pulmonary edema using a two dimensional theoretical model of the thorax" by Keren Horman and Shimon Abboud, and "Assessment of cardiac stroke volume in patients with implanted cardiac pacemaker using parametric electrical impedance tomography: A theoretical 2D study" by Muhammad Mhajna and Shimon Abboud, a reconstructed parameter was a real conductivity of the tissue, Upon application of a quasi-static approximation, according to the above-mentioned articles, the ratio $$\left|\frac{j\omega\varepsilon}{\sigma}\right| \ll 1$$

was negligible, hence the capacitance effect was neglected. Since edema influences mostly the real conductivity, σ, the quasi-static approximation was appropriate.

In some embodiments of the present application, relative permittivity (or the specific capacitance) of bone is more significantly affected by changes in bone mineral density in comparison to the real conductivity. In an above-mentioned study by Williams and Saha (1996) it was found that the relationship between the specific capacitance ($C_{sp}$) and the bone density ($\rho_w$) is $C_{sp} \propto \rho_w^{2.25}$. On the other hand, the specific resistivity ($R_{sp}$) changed linearly with bone density, $R_{sp} \propto \rho_w$. In order to account for these differences, the equations used in some embodiments of the method account for both conductivity and permittivity of the bone tissue. The accounting for both is optionally done by replacing real conductivities (in Equation 2 above) with complex conductivities, defined by $$\sigma^* = \sigma + j\frac{2\pi}{f}\varepsilon_r\varepsilon_0.$$

The voltage measurements optionally include both magnitude and phase measurements which translated into the complex conductivity.

Also, in the above-mentioned articles relating to pulmonary edema, a driving frequency is 20 kHz, and in some embodiments of the present application, the driving frequency is optionally ~100 kHz, which potentially improves accounting for both conductivity and permittivity of bone tissue.

Computerized Simulations

Computerized simulations have been made using a 3D model of the human body (XCAT Phantom). In the model, the thigh was segmented into two main tissue types; bone and body tissue. The conductivity of the bone was taken as an average of the conductivities of three bone tissues, and the conductivity of body tissue was taken as an average of the conductivity of fat, muscle and skin.

Figure 1A:
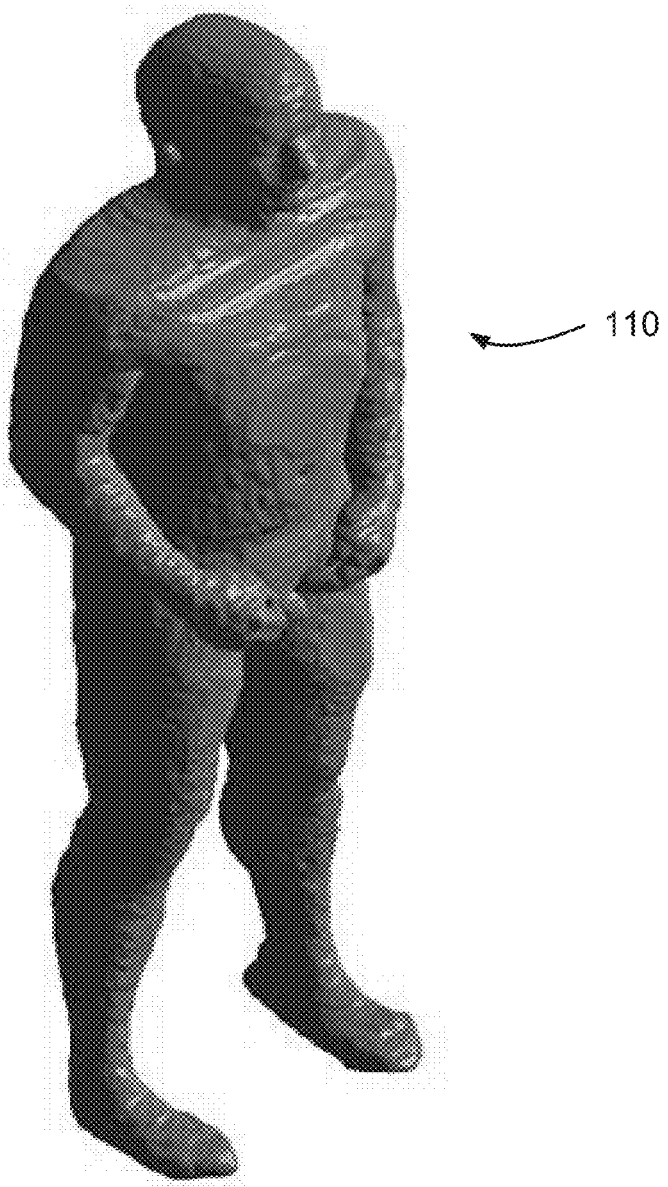

Reference is now made to FIG. 1A, which is a simplified illustration of a full 3D phantom model 110 used in computerized simulations according to an example embodiment of the invention.

Figure 1B:
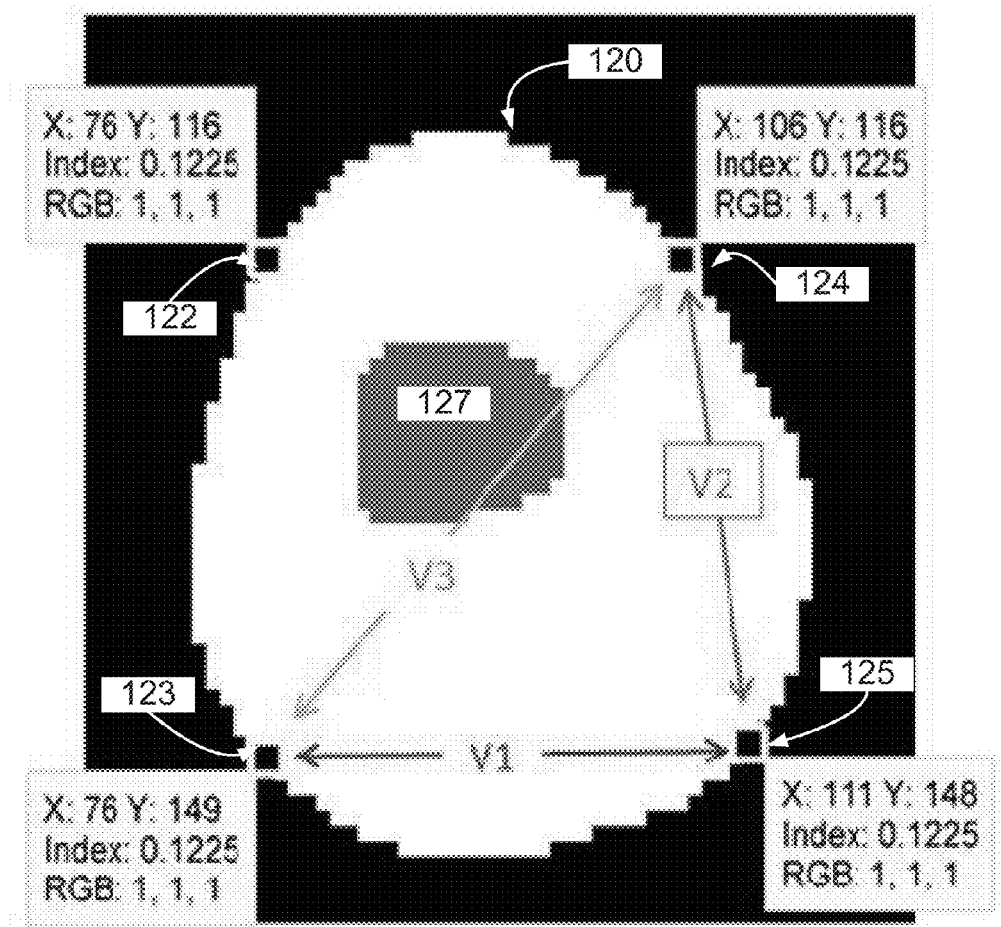

Reference is now made to FIG. 1B, which is a simplified illustration of a cross section 120 of the thigh of the phantom 110 of FIG. 1A, along with positions of electrodes 122 123 124 125 used in the simulations and in the potential measurements.

FIG. 1B depicts the cross section 120 of an example thigh of the phantom 110 of FIG. 1A, along with optional positions for electrodes 122 123 124 125.

In some embodiments the electrodes are optionally placed such that at least one straight line path between a pair of electrodes goes through a bone 127. A non-limiting example of such a pair of electrodes is the pair which includes electrode 123 and electrode 124, depicted in FIG. 1B as V3.

In some embodiments the electrodes are optionally placed at locations which are optionally sensitive to changes in BMD. In such embodiments a relative location of the electrodes is optionally changed in simulations so as to capture relative location which are sensitive to changes in BMD.

In some embodiments the electrodes are optionally placed such that at least one straight line path between a pair of electrodes does not go through the bone 127. Two non-limiting examples of such pairs of electrodes are the pair which includes electrode 123 and electrode 125, depicted in FIG. 1B as V1, and the pair which includes electrode 124 and electrode 125, depicted in FIG. 1B as V2.

In some embodiments four electrodes 122 123 124 125 are placed in four approximately equal spaced positions around a circumference of the body part being measured, in the example of FIG. 1B it is the thigh 120.

In the example embodiment of FIG. 1B, electrode 122 was used to inject current. In a first simulation current was injected from electrode 122 to electrode 124 and V1 was measured. In a second simulation current was injected from electrode 122 to electrode 123 and V2 was measured. In a third simulation current was injected from electrode 122 to electrode 125 and V3 was measured.

In some embodiments more electrodes may optionally be placed around a body part. In some embodiments two or more electrodes may optionally be used to inject current.

In some embodiments one or more electrodes are optionally placed to measure potential differences across a body part such the current path between an injection electrode and a pickup electrode mostly includes muscle and/or fat and other electrodes are placed such the current path between an injection electrode and a pickup electrode includes more bone.

Results of the simulations are shown below in Table 1. Three surface potentials V1, V2 and V3 were calculated, which correspond to measuring surface potentials in an actual patient, for each value of BMD.

TABLE 1

Relative change in potential as a function of a relative change in Bone Mineral Density.

| Relative change in voltage [%] | | | |
| --- | --- | --- | --- |
| 3rd measurement | 2nd measurement | 1st measurement | BMD $\left[\frac{gm}{cm^3}\right]$ |
| 0* | 0* | 0* | 0.1666 |
| −1.7544 | −2.1829 | −2.2967 | 0.1851 |
| −3.4319 | −4.4291 | −4.6941 | 0.2036 |
| −4.9982 | −6.7039 | −7.1571 | 0.2222 |
| −6.4312 | −8.978 | −9.6546 | 0.2407 |
| −7.7197 | −11.2275 | −12.1596 | 0.2592 |
| −8.8611 | −13.4341 | −14.6492 | 0.2777 |
| −9.8602 | −15.5837 | −17.1045 | 0.2963 |
| −10.7263 | −17.6665 | −19.5106 | 0.3148 |
| −11.472 | −19.6757 | −21.8555 | 0.3333 |

*indicates baseline results:

The BMD column of Table 1 indicated BMD values, in units of gm/cm$^3$, which were used in the model depicted in FIG. 1B. The three columns titled "1$^{st}$ measurement", "2$^{nd}$ measurement" and "3$^{rd}$ measurement" correspond to potentials modeled for V1, V2 and V3 depicted in FIG. 1B for the BMD values used. The values in the three columns show a relative change in potential (voltage) in percent, relative to a baseline measure where a BMD of 0.1666 gm/cm$^3$ was modeled.

TABLE 2

Reference potential measurements which serve as baseline results for Table 1.

| V3 [Volt] | V2 [Volt] | V1 [Volt] | Conductivity $\left[\frac{s}{m}\right]$ | BMD $\left[\frac{gm}{cm^3}\right]$ |
|---|---|---|---|---|
| 0.0900 | 0.4286 | 0.3387 | 0.0174 | 0.1666 |

Figure 2:
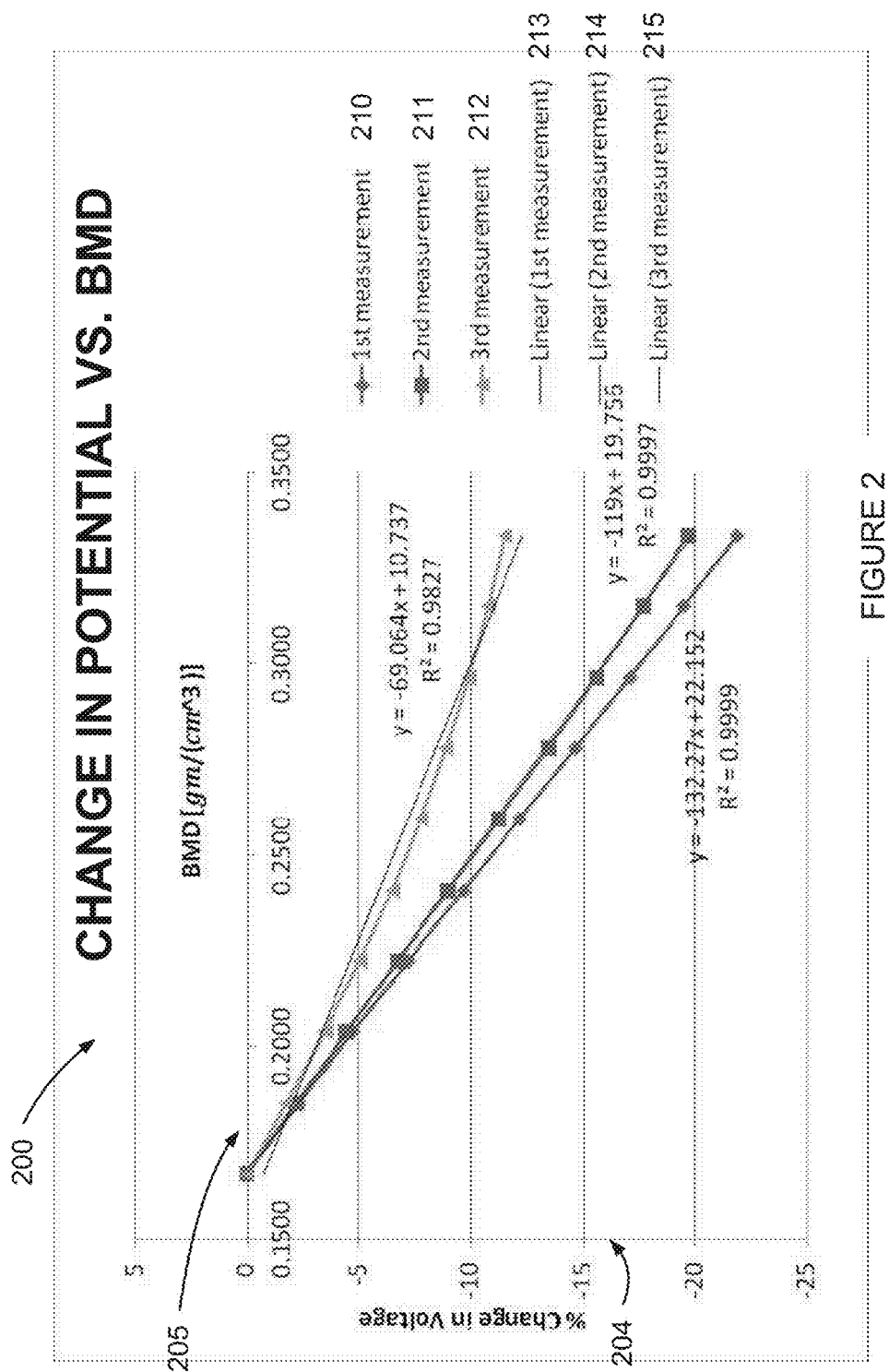

Reference is now made to FIG. 2, which is a graph 200 depicting the results of computer simulations of an example embodiment of the invention.

The graph of FIG. 2 depicts the results of the simulations of Table 1. The graph of FIG. 2 depicts a relative change in the surface potential as a function of Bone Mineral Density.

The graph 200 includes an X-axis 205 corresponding to BMD, in units of gm/cm$^3$. The actual BMD values may also be seen in Table 1. The graph 200 includes a Y-axis 204 corresponding to a relative change in potential, in units of percent, as described above with reference to Table 1.

The graph 200 depicts three sets of measurements 210 211 212. A first set of measurements 210 corresponds to the 1$^{st}$ measurement V1 of Table 1; a second set of measurements 211 corresponds to the 2nd measurement V2 of Table 1; and a third set of measurements 212 corresponds to the 3$^{rd}$ measurement V3 of Table 1.

The graph 200 also depicts three linear approximations 213 214 215 of the three sets of measurements 210 211 212 correspondingly.

The graph 200 also includes equations defining the linear approximations 213 214 215 of each one of the three sets of measurements 210 211 212, and R$^2$ values of the linear approximations 213 214 215 indicating the sets of measurements 210 211 212 are indeed very close to their linear approximations 213 214 215.

The simulation results suggest that there is a correlation between the BMD and the surface potential. A change in BMD causes a linear change in the surface electrical potential. A slope of a linear fitted curve is approximately −110 [% change in Volts/BMD units], which means that a 10% change in the BMD will cause an 11% change in the surface potential (approximately). From the results we can see also that the relation between the BMD and the surface potential is affected by the position of the bone inside the body. In FIG. 2 V1 shows most sensitivity to a change in BMD, the potential being measured when current was injected from electrode 122 to electrode 124.

Figure 3:
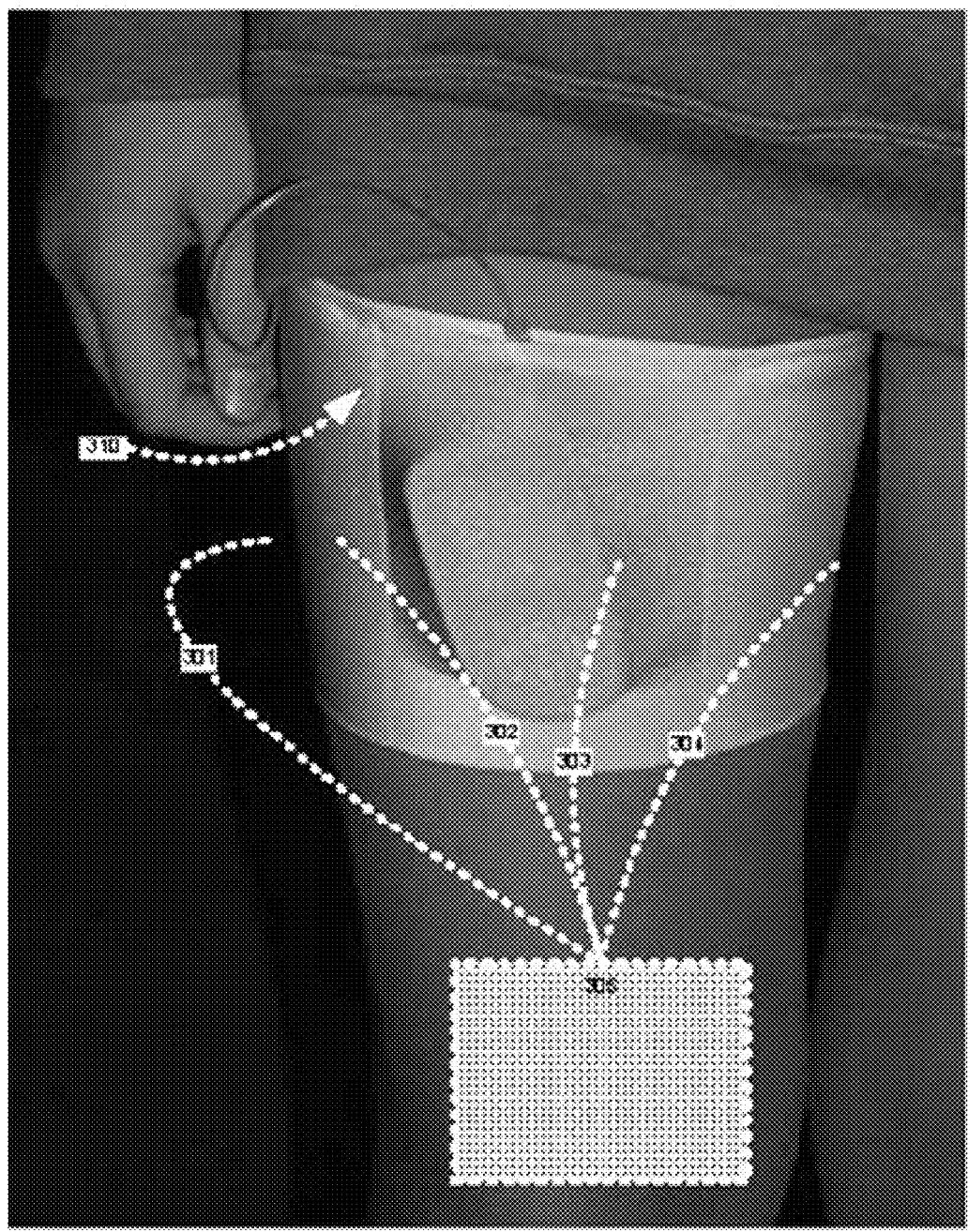

Reference is now made to FIG. 3, which is a simplified illustration of an example embodiment of the invention.

FIG. 3 depicts a thigh, upon which four electrodes are attached, using four electric conductors 301 302 303 304. The electric conductors 301 302 303 304 are connected to an electronics box 305, which provides current for injection into injection electrodes, and measures electric potential at pickup electrodes.

In the example embodiment depicted in FIG. 3 the pickup electrodes are optionally attached approximately equidistant circumferentially around the thigh, at opposite corners, to electric conductors 302 304, and the injection electrodes are optionally attached at opposite corners, to electric conductors 301 303.

FIG. 3 depicts an optional sleeve 310, or cuff, which optionally slides over the thigh and optionally maintains the locations of the electrodes.

In some embodiments the electronics box 305 is self-powered, produces current for injection and operation of the electronics box 305, and records the electric potential measurements. Measurements recorded by the electronics box 305 are optionally transferred to an analysis unit (not shown) for calculating bone conductance.

In some embodiments the electronics box 305 is connected to an external source of power, produces current for injection and operation of the electronics box 305, and records the electric potential measurements. Measurements recorded by the electronics box 305 are optionally transferred to an analysis unit (not shown) for calculating bone conductance.

In some embodiments the electronics box 305 produces current for injection and operation of the electronics box 305, and measures the electric potential measurements. The measurements are optionally transferred to an analysis unit (not shown) for calculating bone conductance.

In some embodiments the electronics box 305 represents a unit which, whether externally powered or self-powered, produces current for injection and operation of the electronics box 305, measures the electric potential measurements and performs the calculating of bone conductance.

In summary, the pEIT technique can be used as a BMD monitoring method. Some uses of pEIT based systems are to detect low BMD before a fracture occurs, to confirm a diagnosis of low BMD if a patient has a fracture already, to predict a patient's probability of fracturing in the future, to determine the patient's rate of bone loss, and to monitor the effects of treatment if BMD measurements are conducted at intervals.

Figure 4:
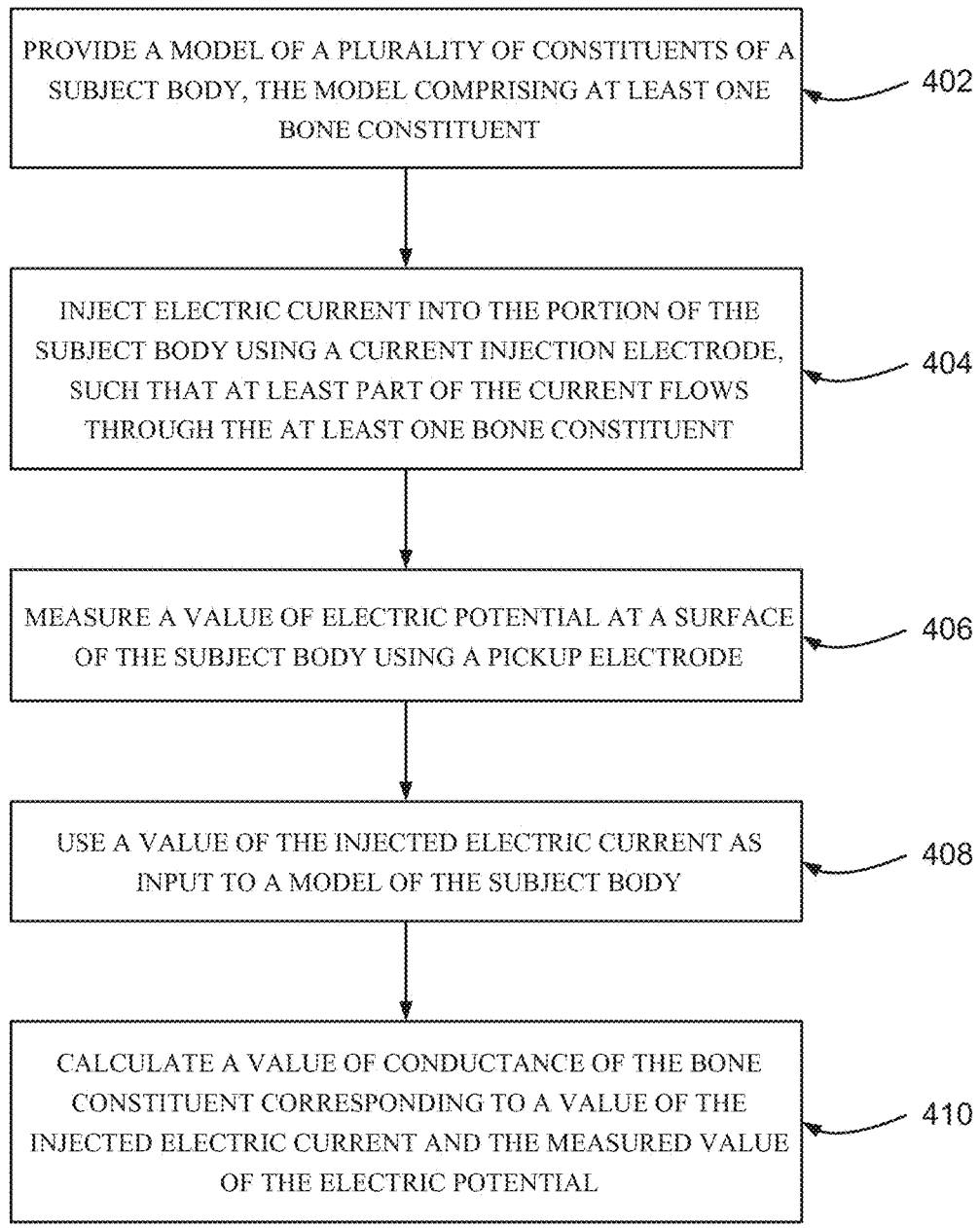

Reference is now made to FIG. 4, which is a simplified flow chart illustration of a method of measuring bone conductance according to an example embodiment of the invention.

The example method of FIG. 4 includes:

providing a model of a plurality of constituents of at least a portion of a subject body, the model comprising at least one bone constituent (402);

injecting electric current into the portion of the subject body using a current injection electrode, such that at least part of the current flows through the at least one bone constituent (404);

measuring a value of electric potential at a surface of the subject body using a pickup electrode (406);

using a value of the injected electric current as input to a model of the at least a portion of a subject body (408); and calculating a value of conductance of the bone constituent corresponding to a value of the injected electric current and the measured value of the electric potential (410).

An Additional Example Embodiment of a Three-Dimensional Human Model and Osteoporosis Simulation An additional example embodiment is now described. For a spatial three-dimensional model, a three-dimensional phantom of a male's body was acquired. A 4D XCAT Phantom was based on tagged MRI images as well as high-resolution CT images. The phantom provides a realistic model of human anatomy in four dimensions, (three dimension plus time) modeling respiratory and cardiac motions. In the present description of the example embodiment nondynamic calculation was performed, hence the phantom was used in 3D, whereas the fourth dimension of the change in time was not in use in the example embodiment.

The phantom was sampled into 128×128×350 pixels. The phantom was segmented into different tissue types, each tissue type assigned with its appropriate electrical conductivity at an excitation frequency of 20 kHz, as described in above-mentioned Gabriel 1996, and as depicted below in Table 3.

TABLE 3

Electrical conductivity values for varying tissues at 20 kHz excitation frequency

| Tissue | Conductivity [S/m] |
| --- | --- |
| Airway | 0.3186 |
| Blood | 0.7 |
| Blood vessel | 0.31466 |
| Body activity (fat, muscle, skin) | 0.1421 |
| Bone marrow | 0.002896 |
| Brain | 0.12 |
| Cancellous bone (spine) | 0.0829 |
| Cartilage | 0.17626 |
| Cortical bone | 0.020513 |
| Heart | 0.1718 |
| Kidney | 0.14671 |
| Large intestine | 0.21462 |
| Liver | 0.0607 |
| Long | 0.07 |
| Prostate | 0.4314 |
| Rectum | 0.345 |
| Small intestine | 0.568 |
| Spinal cord | 0.053518 |
| Spleen | 0.114 |
| Stomach | 0.53134 |

The phantom section used for the simulation of the example embodiment was a partial area of a body centre, an area which includes the lower back, restricted to an area of 128*128*41 pixels.

Figure 5B:
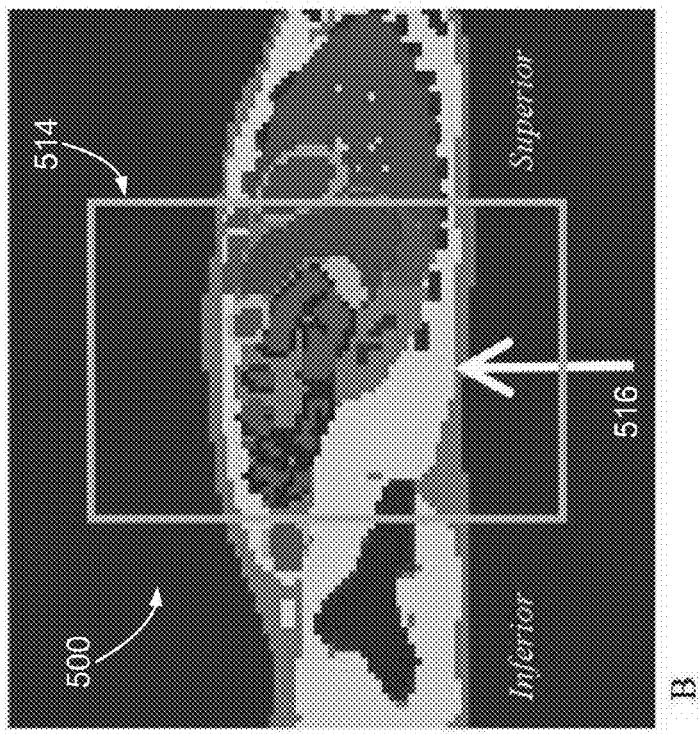
Figure 5A:
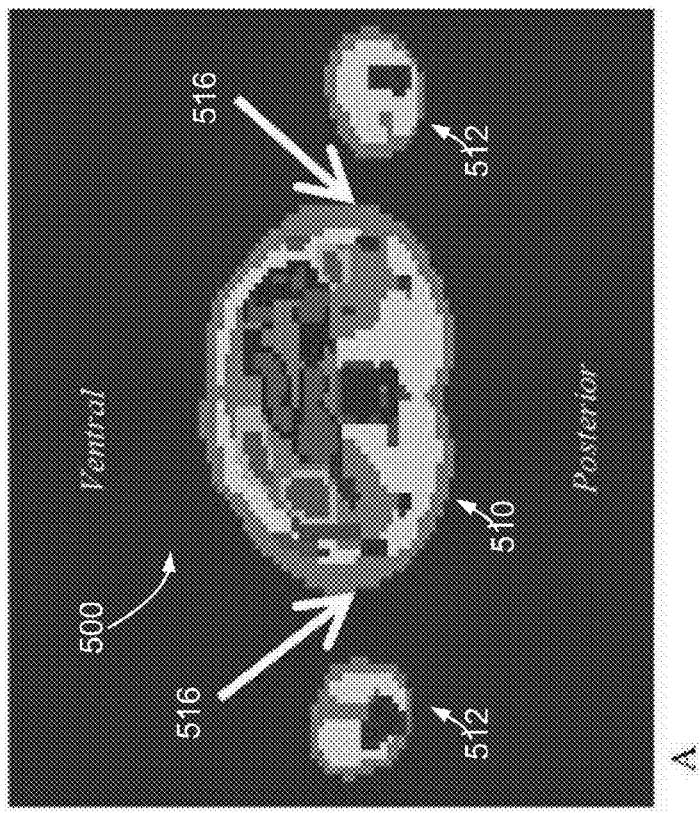

Reference is now made to FIGS. 5A and 5B, which are a top view cross section and a side view cross section respectively of a phantom 500 according to an example embodiment of the invention.

FIG. 5A depicts the top view cross section of the phantom 500 at a back section, showing a cross section of the back 510 and cross sections 512 of two arms.

FIG. 5B depicts the side view cross section of the phantom 500, showing a frame 514 which delineates the partial area mentioned above as used in the simulation.

Surface electrodes were simulated, both current injection electrodes and measuring electrodes.

In the example embodiment depicted in FIGS. 5A and 5B, two current injecting electrodes 516 were placed on the lower back orientation, placed on the body sides (waists) as depicted in FIG. 5A. The electrodes 516 were placed on the body posterior part.

Figure 5C:
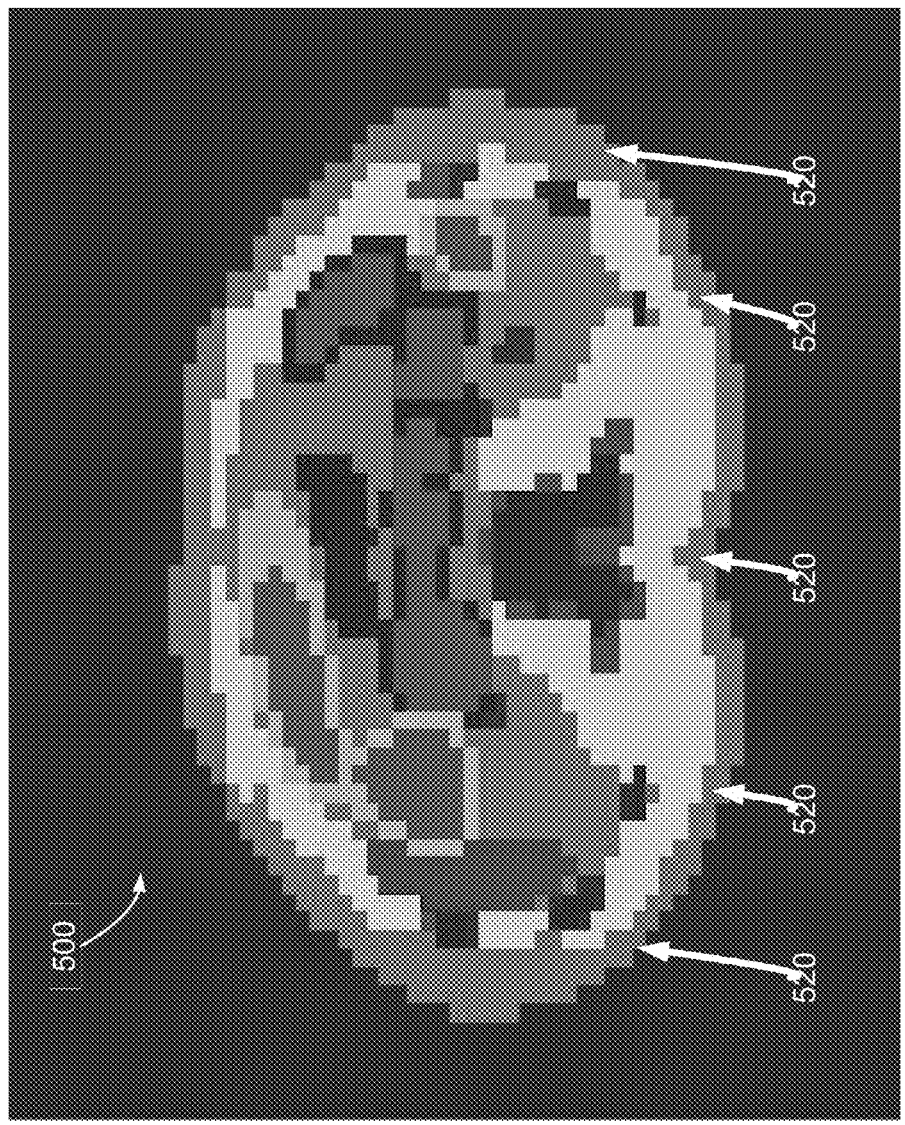

Reference is now made to FIG. 5C, which is a top view cross section of the phantom 500 of FIGS. 5A and 5B. FIG. 5C depicts locations of the measuring electrodes 520 on the 3D phantom 500.

Figures 6A, 6B:
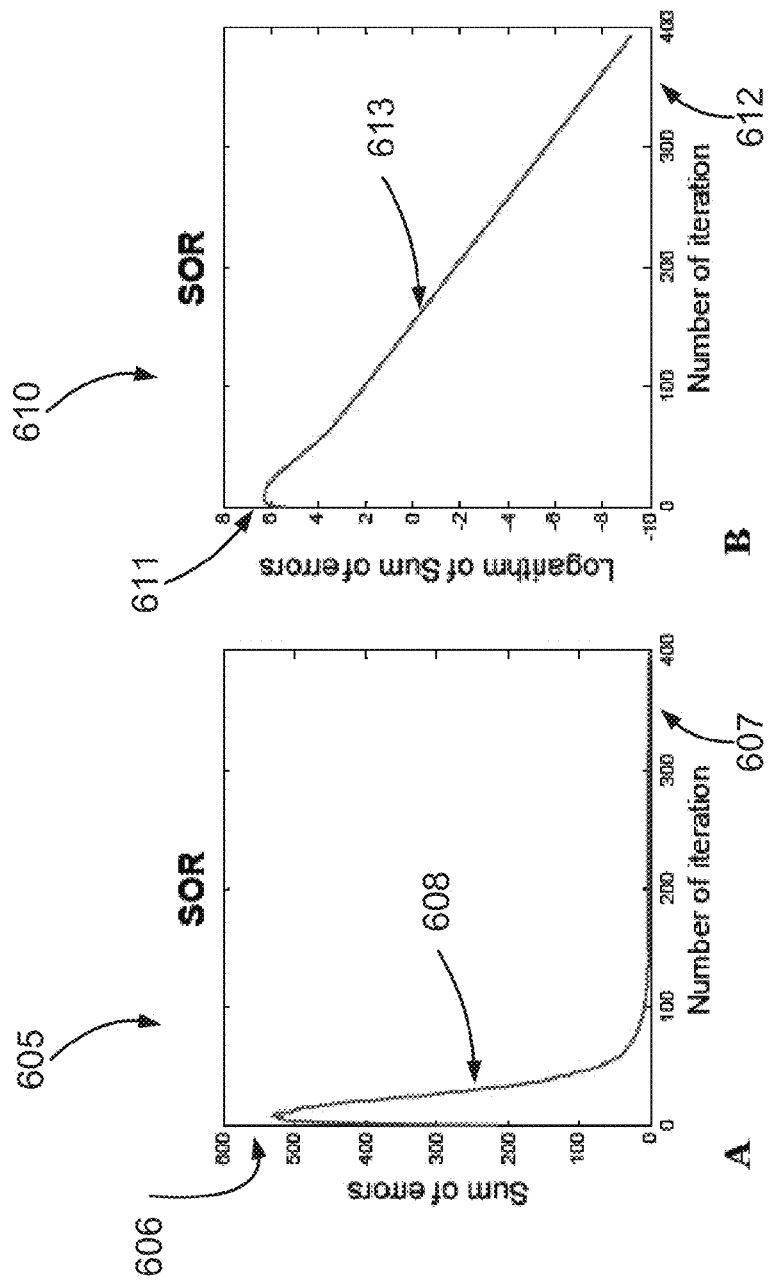

In the example embodiment of FIGS. 5A,B,C five measuring electrodes 520 were placed on the lower back orientation, approximately at a same height along the torso as the current injection electrodes 516 shown in FIG. 6B, spread along a posterior part of the body, as depicted in FIG. 5C.

In an example embodiment of simulating a varied spinal BMD, potentially as an indication for a disease stage, varied bone relative permittivity values were set.

TABLE 4

Permittivity values at 20 kHz excitation frequency, set for simulating a varying spinal BMD

| Simulation | Permittivity Value |
| --- | --- |
| Healthy bone | 1005 (Gabriel 1996) |
| Osteoporotic bone - mild | 200 |
| Osteoporotic bone - severe | 10 |

In the example embodiment described 1,201 pixels in the phantom optionally simulate the spine out of a total number of 83,275 body pixels, which optionally composes 1.44% of the body volume used for the simulation. In the spine pixels the permittivity values were optionally set according to the values of Table 4, whereas in the rest of the body's pixels permittivity values were optionally set to zero, meaning that no permittivity values were set.

In an experimental embodiment a potential (voltage) reading at each measuring electrode was optionally calculated numerically, and optionally compared with readings of other electrodes, and optionally as a function of spinal BMD.

An Example Three-Dimensional Human Model and Osteoporosis Simulation

A simulation of an example three-dimensional human model and osteoporosis is optionally performed by setting up a set of linear equations for a potential inside each cell in a volume of the three-dimensional human model, optionally_depending on conductivity and potential of its six surrounding cells.

Solving the Forward Problem

Solving the Forward Problem optionally starts from an electrical source configuration representing current injecting electrodes. Potentials at measuring electrodes are calculated for this configuration.

In some embodiments, a Successive Over Relaxation (SOR) method is used for numerical solution of the Forward Problem on the geometry of the 3-dimensional human model, also termed phantom.

The error of the SOR method used for the numerical solution of the Forward Problem on the geometry of the 3-dimensional phantom as a function on number of iteration converges to zero, as depicted in FIGS. 6A and 6B.

Reference is now made to FIGS. 6A and 6B, which are graphs describing error convergence of the SOR method in an example embodiment of the invention.

FIG. 6A depicts a graph 605 with a Y-axis 606 proportional to the sum of errors, and an X-axis 607 proportional to an iteration number. A line 608 depicts the sum of errors converging to zero as the number of iterations rise.

FIG. 6B depicts a graph 610 with a Y-axis 611 proportional to the sum of errors, and an X-axis 612 proportional to an iteration number. A line 613 depicts the logarithm of the sum of errors converging to zero as the number of iterations rise.

Figures 7A, 7B:
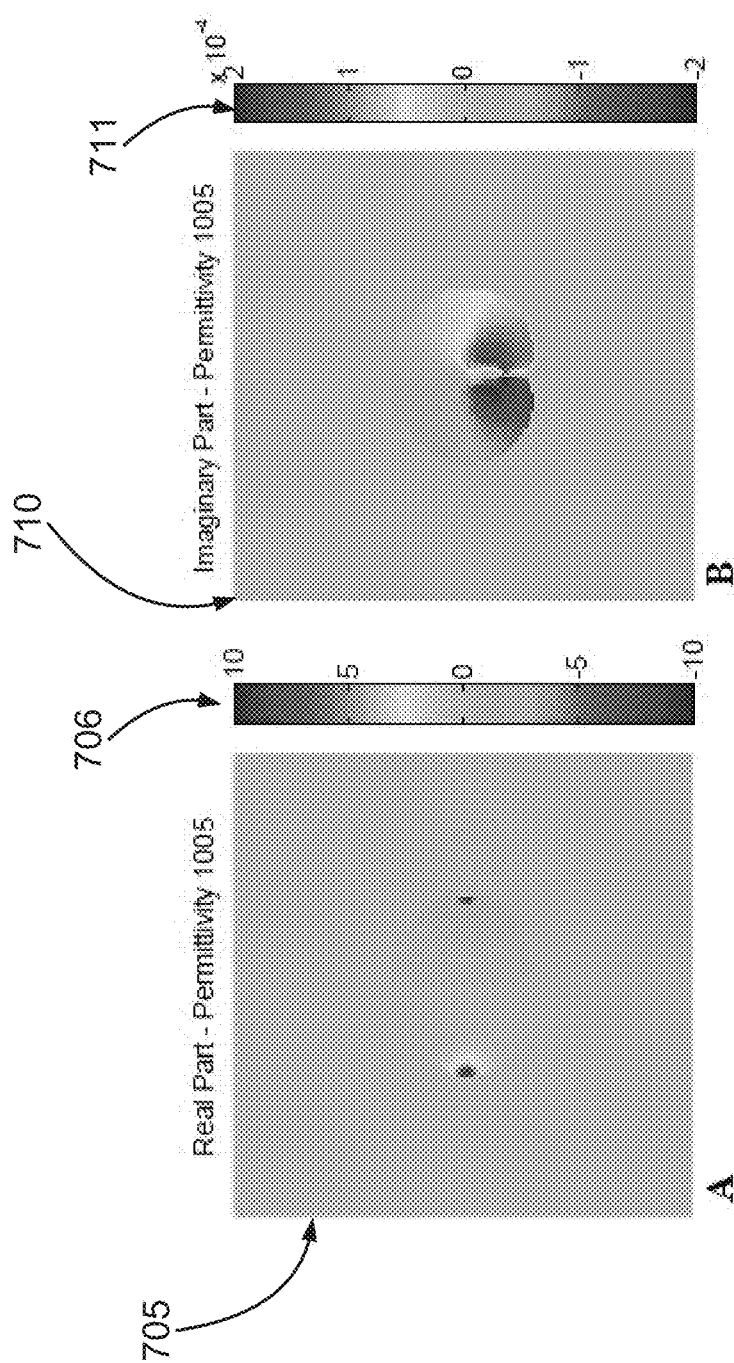

A potential map resulting from the example of the simulation on the phantom with permittivity set to 1005, which simulates healthy bone, where current injection is simulated along the middle body section is presented in FIGS. 7A and 7B.

Reference is now made to FIGS. 7A and 7B, which are potential maps showing a real part of a potential and an imaginary part of a potential simulated in the example embodiment of FIGS. 6A and 6B.

FIG. 7A depicts a real part of potential map 705 of a lateral cross section of the phantom, and a real part potential scale 706 depicting color change proportional to real part potential.

FIG. 7B depicts an imaginary part of potential map 710 of the lateral cross section of the phantom, and an imaginary part potential scale 706 depicting color change proportional to imaginary part potential.

Comparison of Measuring Electrode Readings

Figures 8A, 8B:
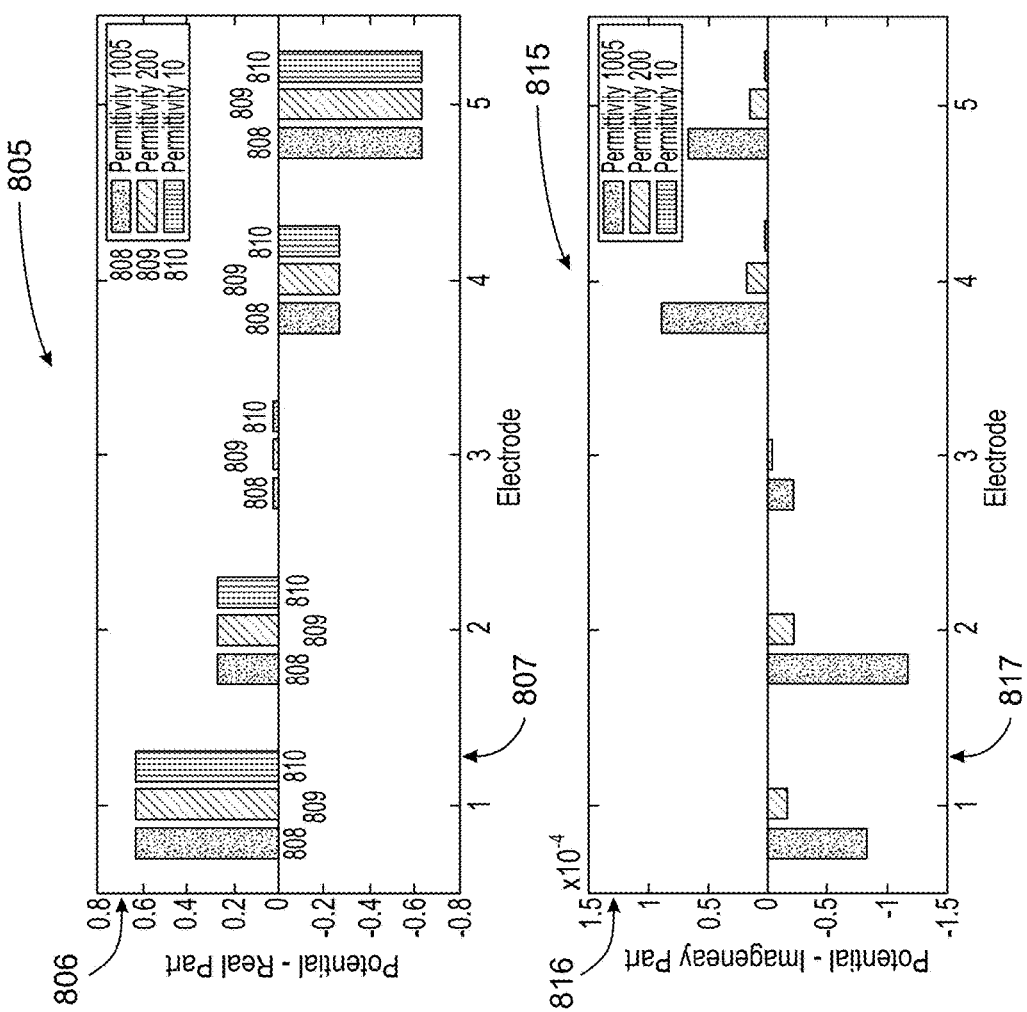

An example of an electric potential calculated by simulation for three different permittivity values as measured by five electrodes is presented in FIGS. 8A and 8B. The electric potential values measured are optionally complex numbers, so FIGS. 8A and 8B depict real and imaginary components.

Reference is now made to FIGS. 8A and 8B, which are graphs showing a real part of a potential and an imaginary part of a potential simulated in an example embodiment of the invention.

FIG. 8A depicts a graph 805 with a Y-axis 806 proportional to a real component of potential, in units of volts, and an X-axis 807 proportional to an electrode number. Colored bars 808 809 810 depicts results from three simulations, having bone permittivity of 1005, 200 and 10 respectively.

FIG. 8B depicts a graph 815 with a Y-axis 816 proportional to an imaginary component of potential, in units of $10^{-4}$ volts, and an X-axis 817 proportional to an electrode number, from 1 to 5. Colored bars 818 819 820 depict results from three simulations, having the same bone permittivity of 1005, 200 and 10 respectively.

Figures 9A, 9B:
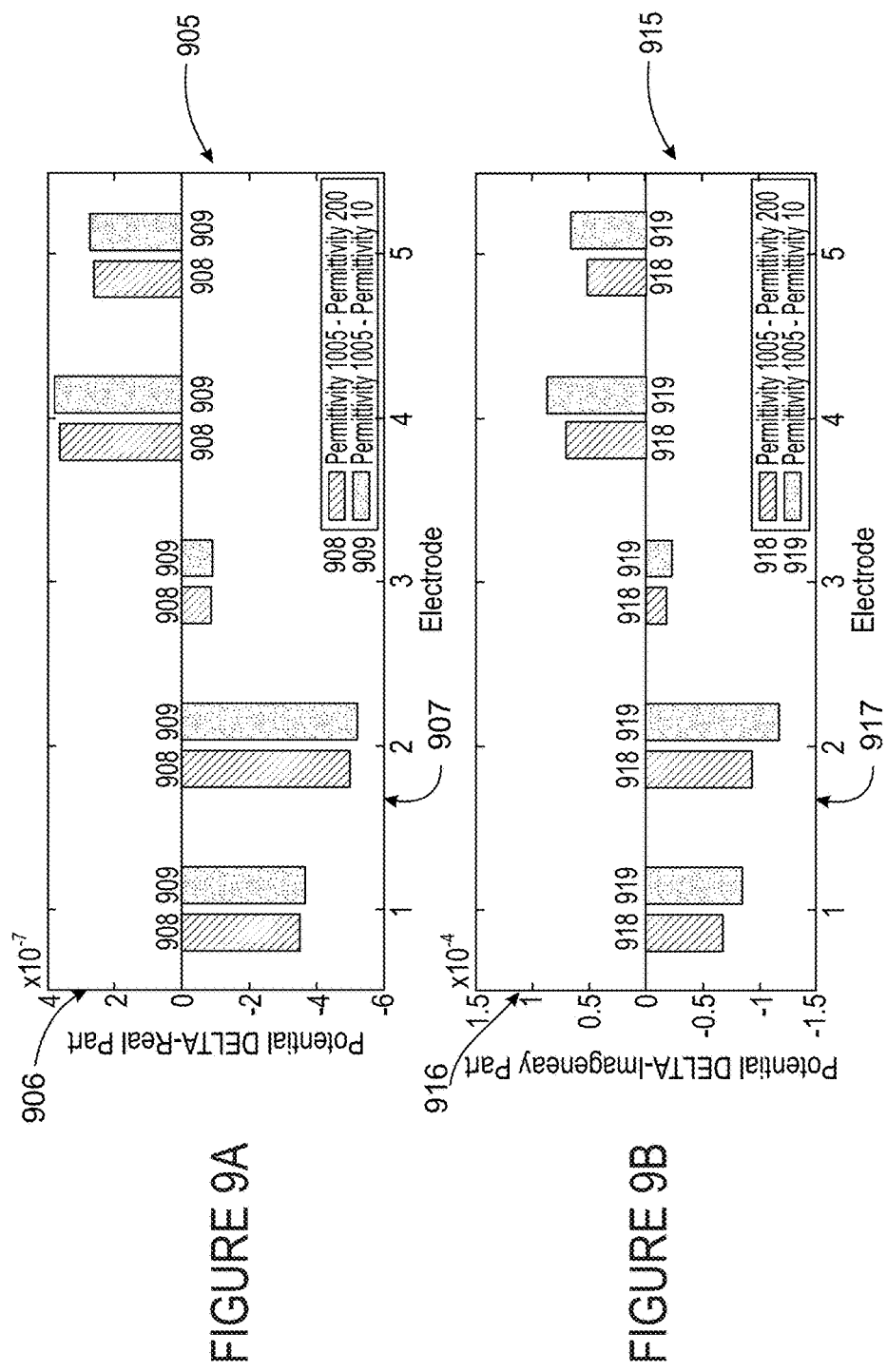

A comparison of electric potential between the simulations of healthy bone (permittivity of 1005) and mild osteoporosis (permittivity of 200) and of healthy bone (permittivity of 1005) and severe osteoporosis (permittivity of 10) as measured by five electrodes is presented in FIGS. 9A and 9B, in real and imaginary component deltas respectively.

Reference is now made to FIGS. 9A and 9B, which are graphs showing a real part of a potential delta and an imaginary part of a potential delta in comparisons of healthy bone to osteoporotic bone simulated in an example embodiment of the invention.

FIG. 9A depicts a graph 905 with a Y-axis 906 proportional to a delta of a real component of potential, in units of $10^{-7}$ volts, and an X-axis 907 proportional to an electrode number. Colored bars 908 909 depict results from two comparisons, a first comparison corresponding to bar 908 being between bone permittivity of 1005 and bone permittivity of 200, and a second comparison corresponding to bar 909 being between bone permittivity of 1005 and bone permittivity of 10.

FIG. 9B depicts a graph 915 with a Y-axis 916 proportional to a delta of an imaginary component of potential, in units of $10^{-4}$ volts, and an X-axis 917 proportional to an electrode number. Colored bars 918 919 depict results from two comparisons, a first comparison corresponding to bar 918 being between bone permittivity of 1005 and bone permittivity of 200, and a second comparison corresponding to bar 919 being between bone permittivity of 1005 and bone permittivity of 10.

FIGS. 9A and 9B depict real (9A) and imaginary (9B) components of differences between a reading of potential at a permittivity of 1005 and the permittivity of 200 (908 918) and permittivity of 1005 and permittivity of 10 (909 919). The potential is compared per measuring electrode, numbered from 1 to 5.

Discussion

An indication for disease stage, as potentially discovered by varied bone relative permittivity values, can be noticed both in real and imaginary components of the potential map. The change in the real part is in the order of $10^{-7}$, and the change in the imaginary part is larger, in the order of $10^{-4}$.

Reference is now made to FIG. 10, which is simplified block diagram of an example embodiment of the invention.

FIG. 10 depicts an electronics unit 1010, attached to one or more current injection electrode(s) 1014, and several potential pickup electrodes 1016.

In some embodiments, the electrodes 1014 1016 are active electrodes.

In some embodiments, the electrodes 1014 1016 are removable from the electronics unit 1010, in some even disposable.

The electronics unit 1010 includes a power unit 1012 to provide power to the injection electrode(s) 1014.

The electronics unit 1010 includes a measurement unit 1018 to measure potential of the pickup electrode(s) 1016.

In some embodiments the electronics unit 1010 optionally includes one or more of the following:

an analysis unit 1022 to analyze data or signals from the measurement unit 1018;

an optional input/output I/O unit 1024 to accept input such as body part being measured, electrode configuration, electrode location, injected current, frequency, and other such parameters as described herein affecting calculation;

a control unit 1020 to control the other units in the electronics unit 1010.

In some embodiments an optional attachment device 1026 is included, in order to attach electrodes to a body part and/or in order to maintain a specific electrode geometry when attaching the electrodes.

Reference is now made to FIGS. 11A and 11B, which are simplified flow chart illustrations of example embodiments of the invention.

FIG. 11A depicts a method of calculating BMD including:

attaching electrodes to a subject (1102); in some embodiments the attaching is optionally done using a sleeve as described above;

inputting setup parameters (1104); the setup parameters optionally include parameters which vary from one measurement to another, while some parameters may be set up in advance;

injecting current (1106);

measuring potential (1108) at several electrode locations; and calculating BMD (1110).

FIG. 11B depicts a method of calculating BMD including:

attaching electrodes to a subject (1122); in some embodiments the attaching is optionally done using a sleeve as described above;

inputting setup parameters (1124); the setup parameters optionally include parameters which vary from one measurement to another, while some parameters may be set up in advance;

injecting current (1126);

measuring potential (1128) at several electrode locations; and calculating BMD (1130);

repeating the above after a period of time (1132);

comparing BMD calculated at different times (1134).

As used herein the term "about" refers to ±20%.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of measuring Bone Mineral Density (BMD) comprising:
    providing an Electrical Impedance Tomography (EIT) conductivity distribution model of a plurality of constituents of at least a portion of a subject body, the model comprising at least one bone constituent;
    injecting electric current into the portion of the subject body using a current injection electrode, such that at least part of the current flows through the at least one bone constituent;
    measuring a value of electric potential at a surface of the subject body using a pickup electrode;
    using a value of the injected electric current as input to the EIT model of the at least a portion of the subject body; and
    calculating a value of conductance of the bone constituent corresponding to a value of the injected electric current and the measured value of the electric potential, the calculating comprising using the EIT conductivity distribution model including at least a bone conductivity value and a value for non-bone tissue conductivity; and
    calculating a patient's Bone Mineral Density (BMD) based on the value of conductance of the bone constituent,
    in which the calculating a value of conductance of the bone constituent includes:
    (a) providing an initial bone conductivity value for use as a bone conductivity value for bone being measured;
    (b) generating said conductivity distribution model including the bone conductivity value and including the values for non-bone tissue conductivity;
    (c) forward calculating a value of electric potential at the pickup electrode;
    (d) minimizing a difference between the value calculated according to step (c) and the value of electric potential measured at the pickup electrode by adjusting the bone conductivity value; and
    (e) calculating a value of conductance of the bone constituent based on the adjusted bone conductivity value.

2. The method of claim 1 in which the EIT model is a parametric EIT (pEIT) model.

3. The method of claim 1 and further comprising calculating Bone Mineral Density (BMD) of the bone constituent based, at least in part, on the value of conductance of the bone constituent.

4. The method of claim 1 in which:
    the injecting electric current into the body using a current injection electrode comprises injecting electric current into the body using a plurality of current injection electrodes; and
    the measuring a value of electric potential at a surface of the body using a pickup electrode comprises measuring a plurality of values of electric potential at the surface of the body using a plurality of pickup electrodes.

5. The method of claim 1 in which the bone constituent comprises a long bone.

6. The method of claim 4 in which the plurality of current injection electrodes are arranged in an arrangement selected from a group consisting of:
a line along the bone constituent;
an array adjacent to the bone constituent; and
a ring adjacent to the bone constituent.

7. The method of claim 4 in which the plurality of pickup electrodes are arranged in an arrangement selected from a group consisting of:
a line along the bone constituent;
an array adjacent to the bone constituent; and
a ring adjacent to the bone constituent.

8. The method of claim 1 in which:
the value calculated in (c) comprises a vector comprising a plurality of values calculated according to (c);
the value of the electric potential measured comprises a vector comprising a plurality of values of electric potential measured at a plurality of pickup electrodes; and
the minimizing a difference between the value calculated in (c) and the value of electric potential measured at the pickup electrode by adjusting the bone conductivity value comprises minimizing a squared difference between the vector comprising a plurality of values calculated according to (c) and the vector comprising a plurality of values of electric potential measured at the plurality of pickup electrodes by adjusting the bone conductivity value.

9. The method of claim 1 in which the calculating bone conductivity value is an iterative calculation including repeating (b) to (d) a plurality of times.

10. The method of claim 9 in which the iterative calculation comprises a Levenberg-Marquardt parametric optimization scheme.

11. The method of claim 1 in which the EIT model comprises a grid selected from a group consisting of:
a grid having a non-cubic shape corresponding to a shape of the portion of the subject body on which measurement is being performed;
a non-Cartesian grid in which grid lines approximately correspond to a shape of the portion of the subject body on which measurement is being performed; and
a non-Cartesian grid in which grid lines approximately correspond to a shape of the bone constituent of the portion of the subject body on which measurement is being performed.

12. The method of claim 1 in which the injected electric current is alternating current and the value of the measured electric potential is a value of a real component of the measured electric potential.

13. A system for measuring Bone Mineral Density (BMD) comprising:

a computational unit which includes an Electrical Impedance Tomography (EIT) conductivity distribution model of a plurality of constituents of at least a portion of a subject, the model comprising at least one bone constituent;
an injection electrode for injecting electric current into the portion of the subject, such that at least part of the current flows through the at least one bone constituent;
a pickup electrode for measuring a value of electric potential at a surface of the subject;
wherein the computational unit:
receives input of what value of the injected electric current is injected into the portion of the subject;
receives input of a measured value of electric potential at the surface of the subject;
uses the value of the injected electric current for input to the model; and
calculates a value of conductance of the bone constituent corresponding to the value of the injected electric current and the measured value of the electric potential, the calculating comprising using the EIT conductivity distribution model including a bone conductivity value and a value for non-bone tissue conductivity; and
calculating a patient's Bone Mineral Density (BMD) based on the value of conductance of the bone constituent,
in which the calculating a value of conductance of the bone constituent includes:
(a) providing an initial bone conductivity value for use as a bone conductivity value for bone being measured;
(b) generating said conductivity distribution model including the bone conductivity value and including the values for non-bone tissue conductivity;
(c) forward calculating a value of electric potential at the pickup electrode;
(d) minimizing a difference between the value calculated according to step (c) and the value of electric potential measured at the pickup electrode by adjusting the bone conductivity value; and
(e) calculating a value of conductance of the bone constituent based on the adjusted bone conductivity value.

14. The system of claim 13 in which the EIT model is a parametric EIT (pEIT) model.

15. The system of claim 13 in which at least one electrode is an active electrode.

16. The system of claim 13 comprising a plurality of injection electrodes and a plurality of pickup electrodes.

17. The system of claim 13 and further comprising a sleeve for sliding over a subject and placing at least some of the electrodes in a defined geometric relation to each other.

18. The system of claim 17 in which at least some of the electrodes are arranged in an arrangement selected from a group consisting of:
a line;
an array; and
a ring.

* * * * *